United States Patent
Blomquist

(10) Patent No.: US 10,943,687 B2
(45) Date of Patent: Mar. 9, 2021

(54) EXPERT SYSTEM FOR INSULIN PUMP THERAPY

(71) Applicant: Tandem Diabetes Care, Inc., San Diego, CA (US)

(72) Inventor: Michael L. Blomquist, Blaine, MN (US)

(73) Assignee: Tandem Diabetes Care, Inc., San Diego, CA (US)

( * ) Notice: Subject to any disclaimer, the term of this patent is extended or adjusted under 35 U.S.C. 154(b) by 0 days.

(21) Appl. No.: 16/507,380

(22) Filed: Jul. 10, 2019

(65) Prior Publication Data

US 2019/0328967 A1    Oct. 31, 2019

Related U.S. Application Data

(63) Continuation of application No. 14/962,635, filed on Dec. 8, 2015, now Pat. No. 10,357,607, which is a
(Continued)

(51) Int. Cl.
| | |
|---|---|
| *G16H 20/17* | (2018.01) |
| *G16H 50/20* | (2018.01) |
| *A61M 5/142* | (2006.01) |
| *A61M 5/172* | (2006.01) |
| *G16H 40/63* | (2018.01) |
| *G05B 15/02* | (2006.01) |
| *G06N 5/02* | (2006.01) |
| *G16H 10/60* | (2018.01) |

(52) U.S. Cl.
CPC .......... *G16H 20/17* (2018.01); *A61M 5/142* (2013.01); *A61M 5/14244* (2013.01); *A61M 5/1723* (2013.01); *G05B 15/02* (2013.01); *G06N 5/027* (2013.01); *G16H 10/60* (2018.01); *G16H 40/63* (2018.01); *G16H 50/20* (2018.01); *A61M 2005/1726* (2013.01); *A61M 2205/502* (2013.01); *A61M 2205/507* (2013.01); *A61M 2205/52* (2013.01)

(58) Field of Classification Search
CPC ...... A61M 5/1723; A61M 5/142; A61M 5/14; G16H 20/17; G16H 50/20; G06F 19/3468
See application file for complete search history.

(56) References Cited

U.S. PATENT DOCUMENTS

| | | |
|---|---|---|
| 2,462,596 A | 2/1949 | Bent et al. |
| 2,629,376 A | 2/1953 | Pierre et al. |
| (Continued) | | |

FOREIGN PATENT DOCUMENTS

| | | |
|---|---|---|
| DE | 399065 | 7/1924 |
| DE | 399065 C | 7/1924 |
| (Continued) | | |

OTHER PUBLICATIONS

Application and File History for U.S. Appl. No. 14/684,495, filed Apr. 13, 2015, inventor Blomquist, et al.
(Continued)

*Primary Examiner* — Ronald D Hartman, Jr.
(74) *Attorney, Agent, or Firm* — Patterson Thuente Pedersen, P.A.

(57) ABSTRACT

An apparatus including a controller can determine a rate of change of a blood glucose level of a patient and generate a pump setting based on the rate of change.

19 Claims, 5 Drawing Sheets

Related U.S. Application Data continuation of application No. 14/684,495, filed on Apr. 13, 2015, now Pat. No. 9,474,856, which is a continuation of application No. 13/530,404, filed on Jun. 22, 2012, now Pat. No. 9,008,803, which is a continuation of application No. 12/774,991, filed on May 6, 2010, now Pat. No. 8,219,222, which is a continuation of application No. 11/753,420, filed on May 24, 2007, now Pat. No. 7,751,907.

(56) References Cited

U.S. PATENT DOCUMENTS

| | | |
|---|---|---|
| 2,691,542 A | 10/1954 | Chenoweth et al. |
| 3,059,639 A | 10/1962 | Blackman et al. |
| 4,392,849 A | 7/1983 | Petre et al. |
| 4,393,365 A | 7/1983 | Kondo et al. |
| 4,403,984 A | 9/1983 | Ash et al. |
| 4,475,901 A | 10/1984 | Kraegen et al. |
| 4,538,616 A | 9/1985 | Rogoff |
| 5,000,664 A | 3/1991 | Lawless et al. |
| 5,050,612 A | 9/1991 | Matsumura |
| 5,122,362 A | 6/1992 | Phillips et al. |
| 5,153,827 A | 10/1992 | Coutre et al. |
| 5,181,910 A | 1/1993 | Scanlon |
| 5,207,666 A | 5/1993 | Idriss et al. |
| 5,219,330 A | 6/1993 | Bollish et al. |
| 5,311,175 A | 5/1994 | Waldman |
| 5,338,157 A | 8/1994 | Blomquist |
| 5,362,562 A | 11/1994 | Evans et al. |
| 5,364,346 A | 11/1994 | Schrezenmeir |
| 5,368,562 A | 11/1994 | Blomquist et al. |
| 5,376,070 A | 12/1994 | Purvis et al. |
| 5,389,078 A | 2/1995 | Zalesky et al. |
| 5,395,326 A | 3/1995 | Haber et al. |
| 5,482,446 A | 1/1996 | Williamson et al. |
| 5,485,408 A | 1/1996 | Blomquist |
| 5,497,772 A | 3/1996 | Schulman et al. |
| 5,536,249 A | 7/1996 | Castellano et al. |
| 5,551,850 A | 9/1996 | Williamson et al. |
| 5,558,638 A | 9/1996 | Evers et al. |
| 5,569,186 A | 10/1996 | Lord et al. |
| 5,658,250 A | 8/1997 | Blomquist et al. |
| 5,658,252 A | 8/1997 | Johnson |
| 5,660,163 A | 8/1997 | Schulman et al. |
| 5,665,065 A | 9/1997 | Colman et al. |
| 5,669,877 A | 9/1997 | Blomquist |
| 5,674,240 A | 10/1997 | Bonutti et al. |
| 5,681,285 A | 10/1997 | Ford et al. |
| 5,685,844 A | 11/1997 | Marttila |
| 5,695,473 A | 12/1997 | Olsen |
| 5,713,856 A | 2/1998 | Eggers et al. |
| 5,745,378 A | 4/1998 | Barker et al. |
| 5,782,805 A | 7/1998 | Meinzer et al. |
| 5,810,771 A | 9/1998 | Blomquist |
| 5,814,015 A | 9/1998 | Gargano et al. |
| 5,822,715 A | 10/1998 | Worthington et al. |
| 5,876,370 A | 3/1999 | Blomquist |
| 5,879,143 A | 3/1999 | Cote et al. |
| 5,885,211 A | 3/1999 | Eppstein et al. |
| 5,919,216 A | 7/1999 | Houben et al. |
| 5,935,099 A | 8/1999 | Peterson et al. |
| 5,935,106 A | 8/1999 | Olsen |
| 5,960,403 A | 9/1999 | Brown |
| 6,023,629 A | 2/2000 | Tamada |
| 6,024,539 A | 2/2000 | Blomquist |
| 6,077,055 A | 6/2000 | Vilks |
| 6,122,536 A | 9/2000 | Sun et al. |
| 6,142,939 A | 11/2000 | Eppstein et al. |
| 6,175,752 B1 | 1/2001 | Say et al. |
| 6,233,471 B1 | 5/2001 | Berner et al. |
| 6,241,704 B1 | 6/2001 | Peterson et al. |
| 6,248,057 B1 | 6/2001 | Mavity et al. |
| 6,248,065 B1 | 6/2001 | Brown |
| 6,248,067 B1 | 6/2001 | Causey, III et al. |
| 6,249,717 B1 | 6/2001 | Nicholson et al. |
| 6,255,781 B1 | 7/2001 | Tsumura |
| 6,272,364 B1 | 8/2001 | Kurnik |
| 6,298,254 B2 | 10/2001 | Tamada |
| 6,306,420 B1 | 10/2001 | Cheikh |
| 6,368,272 B1 | 4/2002 | Porumbescu |
| 6,379,301 B1 | 4/2002 | Worthington et al. |
| 6,422,057 B1 | 7/2002 | Anderson |
| 6,424,847 B1 | 7/2002 | Mastrototaro et al. |
| 6,475,180 B2 | 11/2002 | Peterson et al. |
| 6,475,750 B1 | 11/2002 | Han et al. |
| 6,505,059 B1 | 1/2003 | Kollias et al. |
| 6,517,482 B1 | 2/2003 | Elden et al. |
| 6,535,714 B2 | 3/2003 | Melker et al. |
| 6,539,250 B1 | 3/2003 | Bettinger |
| 6,544,212 B2 | 4/2003 | Galley et al. |
| 6,544,229 B1 | 4/2003 | Danby et al. |
| 6,546,269 B1 | 4/2003 | Kurnik |
| 6,551,276 B1 | 4/2003 | Mann et al. |
| 6,553,244 B2 | 4/2003 | Lesho et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,577,899 B2 | 6/2003 | Lebel et al. |
| 6,582,366 B1 | 6/2003 | Porumbescu |
| 6,595,919 B2 | 7/2003 | Berner et al. |
| 6,623,698 B2 | 9/2003 | Kuo |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,114 B1 | 12/2003 | Poulsen et al. |
| 6,659,978 B1 | 12/2003 | Kasuga et al. |
| 6,668,196 B1 | 12/2003 | Villegas et al. |
| 6,687,522 B2 | 2/2004 | Tamada |
| 6,692,456 B1 | 2/2004 | Eppstein et al. |
| 6,694,191 B2 | 2/2004 | Starkweather et al. |
| 6,740,072 B2 | 5/2004 | Starkweather et al. |
| 6,740,075 B2 | 5/2004 | Lebel et al. |
| 6,744,350 B2 | 6/2004 | Blomquist |
| 6,771,250 B1 | 8/2004 | Oh |
| 6,773,412 B2 | 8/2004 | O'Mahony et al. |
| 6,790,198 B1 | 9/2004 | White et al. |
| 6,809,563 B2 | 10/2004 | Schaal |
| 6,809,653 B1 | 10/2004 | Mann et al. |
| 6,810,290 B2 | 10/2004 | Lebel et al. |
| 6,827,702 B2 | 12/2004 | Lebel et al. |
| 6,835,175 B1 | 12/2004 | Porumbescu |
| 6,852,104 B2 | 2/2005 | Blomquist |
| 6,862,466 B2 | 3/2005 | Ackerman |
| 6,872,200 B2 | 3/2005 | Mann et al. |
| 6,873,268 B2 | 3/2005 | Lebel et al. |
| 6,880,564 B2 | 4/2005 | Erickson |
| 6,882,940 B2 | 4/2005 | Potts et al. |
| 6,895,263 B2 | 5/2005 | Shin et al. |
| 6,902,905 B2 | 6/2005 | Burson et al. |
| 6,916,159 B2 | 7/2005 | Rush et al. |
| 6,918,542 B2 | 7/2005 | Silverbrook et al. |
| 6,934,220 B1 | 8/2005 | Cruitt et al. |
| 6,936,029 B2 | 8/2005 | Mann et al. |
| 6,957,655 B2 | 10/2005 | Erickson et al. |
| 6,958,705 B2 | 10/2005 | Lebel et al. |
| 6,966,325 B2 | 11/2005 | Erickson |
| 6,970,742 B2 | 11/2005 | Mann et al. |
| 6,974,437 B2 | 12/2005 | Lebel et al. |
| 6,979,326 B2 | 12/2005 | Mann et al. |
| 6,997,920 B2 | 2/2006 | Mann et al. |
| 6,998,387 B1 | 2/2006 | Goke et al. |
| 6,999,854 B2 | 2/2006 | Roth |
| 7,004,928 B2 | 2/2006 | Aceti et al. |
| 7,011,630 B2 | 3/2006 | Desai et al. |
| 7,022,072 B2 | 4/2006 | Fox et al. |
| 7,024,236 B2 | 4/2006 | Ford et al. |
| 7,025,743 B2 | 4/2006 | Mann et al. |
| 7,033,338 B2 | 4/2006 | Vilks et al. |
| 7,041,082 B2 | 5/2006 | Blomquist et al. |

(56) References Cited

U.S. PATENT DOCUMENTS

| | | |
|---|---|---|
| 7,073,713 B2 | 7/2006 | Silverbrook et al. |
| 7,083,108 B2 | 8/2006 | Silverbrook et al. |
| 7,092,011 B2 | 8/2006 | Silverbrook et al. |
| 7,097,104 B2 | 8/2006 | Silverbrook et al. |
| 7,097,108 B2 | 8/2006 | Zellner et al. |
| 7,098,803 B2 | 8/2006 | Mann et al. |
| 7,109,878 B2 | 9/2006 | Mann et al. |
| 7,150,741 B2 | 12/2006 | Erickson et al. |
| 7,156,808 B2 | 1/2007 | Quy |
| 7,179,226 B2 | 2/2007 | Crothall et al. |
| 7,181,505 B2 | 2/2007 | Haller et al. |
| 7,183,068 B2 | 2/2007 | Burson et al. |
| 7,187,404 B2 | 3/2007 | Silverbrook et al. |
| 7,201,319 B2 | 4/2007 | Silverbrook et al. |
| 7,204,823 B2 | 4/2007 | Estes et al. |
| 7,231,263 B2 | 6/2007 | Choi |
| 7,234,645 B2 | 6/2007 | Silverbrook et al. |
| 7,247,702 B2 | 7/2007 | Gardner et al. |
| 7,251,516 B2 | 7/2007 | Walker et al. |
| 7,254,782 B1 | 8/2007 | Sherer |
| 7,267,665 B2 | 9/2007 | Steil et al. |
| 7,278,983 B2 | 10/2007 | Ireland et al. |
| 7,282,029 B1 | 10/2007 | Poulsen et al. |
| 7,289,142 B2 | 10/2007 | Silverbrook |
| 7,291,107 B2 | 11/2007 | Hellwig et al. |
| 7,295,867 B2 | 11/2007 | Berner et al. |
| 7,307,245 B2 | 12/2007 | Faries, Jr. et al. |
| 7,320,675 B2 | 1/2008 | Pastore et al. |
| 7,324,012 B2 | 1/2008 | Mann et al. |
| 7,341,577 B2 | 3/2008 | Gill |
| 7,347,836 B2 | 3/2008 | Peterson et al. |
| 7,354,420 B2 | 4/2008 | Steil et al. |
| 7,362,971 B2 | 4/2008 | Silverbrook et al. |
| 7,373,083 B2 | 5/2008 | Silverbrook et al. |
| 7,377,706 B2 | 5/2008 | Silverbrook et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,440,806 B1 | 10/2008 | Whitehurst et al. |
| 7,446,091 B2 | 11/2008 | Van |
| 7,460,152 B2 | 12/2008 | Silverbrook et al. |
| 7,464,010 B2 | 12/2008 | Yang et al. |
| 7,471,994 B2 | 12/2008 | Ford et al. |
| 7,475,825 B2 | 1/2009 | Silverbrook et al. |
| 7,483,050 B2 | 1/2009 | Silverbrook et al. |
| 7,483,743 B2 | 1/2009 | Mann et al. |
| 7,491,187 B2 | 2/2009 | Van et al. |
| 7,497,827 B2 | 3/2009 | Brister et al. |
| 7,515,060 B2 | 4/2009 | Blomquist |
| 7,524,045 B2 | 4/2009 | Silverbrook et al. |
| 7,534,226 B2 | 5/2009 | Mernoe et al. |
| 7,547,281 B2 | 6/2009 | Hayes et al. |
| 7,553,281 B2 | 6/2009 | Hellwig et al. |
| 7,556,613 B2 | 7/2009 | Wittmann et al. |
| 7,559,926 B1 | 7/2009 | Blischak |
| 7,569,030 B2 | 8/2009 | Lebel et al. |
| 7,572,789 B2 | 8/2009 | Cowen et al. |
| 7,588,046 B1 | 9/2009 | Erickson |
| 7,591,801 B2 | 9/2009 | Brauker et al. |
| 7,602,310 B2 | 10/2009 | Mann et al. |
| 7,604,593 B2 | 10/2009 | Parris et al. |
| 7,615,007 B2 | 11/2009 | Shults |
| 7,647,237 B2 | 1/2010 | Malave et al. |
| 7,651,489 B2 | 1/2010 | Estes et al. |
| 7,651,845 B2 | 1/2010 | Doyle, III et al. |
| 7,654,976 B2 | 2/2010 | Peterson et al. |
| 7,674,485 B2 | 3/2010 | Bhaskaran et al. |
| 7,676,519 B2 | 3/2010 | McBride et al. |
| 7,678,071 B2 | 3/2010 | Lebel et al. |
| 7,678,762 B2 | 3/2010 | Green et al. |
| 7,678,763 B2 | 3/2010 | Green et al. |
| 7,687,272 B1 | 3/2010 | Buchwald et al. |
| 7,697,967 B2 | 4/2010 | Stafford |
| 7,699,775 B2 | 4/2010 | Desai et al. |
| 7,704,226 B2 | 4/2010 | Mueller, Jr. et al. |
| 7,708,717 B2 | 5/2010 | Estes et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,717,903 B2 | 5/2010 | Estes et al. |
| 7,722,536 B2 | 5/2010 | Goodnow |
| 7,734,323 B2 | 6/2010 | Blomquist et al. |
| 7,751,907 B2 | 7/2010 | Blomquist |
| 7,766,829 B2 | 8/2010 | Sloan et al. |
| 7,766,830 B2 | 8/2010 | Fox et al. |
| 7,768,386 B2 | 8/2010 | Hayter et al. |
| 7,768,408 B2 | 8/2010 | Reggiardo et al. |
| 7,774,145 B2 | 8/2010 | Brauker et al. |
| 7,775,975 B2 | 8/2010 | Brister et al. |
| 7,776,030 B2 | 8/2010 | Estes et al. |
| 7,778,680 B2 | 8/2010 | Goode, Jr. et al. |
| 7,785,313 B2 | 8/2010 | Mastrototaro |
| 7,794,426 B2 | 9/2010 | Briones et al. |
| 7,794,427 B2 | 9/2010 | Estes et al. |
| 7,794,428 B2 | 9/2010 | Estes et al. |
| 7,797,028 B2 | 9/2010 | Goode, Jr. et al. |
| 7,801,582 B2 | 9/2010 | Peyser |
| 7,806,853 B2 | 10/2010 | Wittmann et al. |
| 7,806,854 B2 | 10/2010 | Damiano et al. |
| 7,806,886 B2 | 10/2010 | Kanderian, Jr. et al. |
| 7,811,231 B2 | 10/2010 | Jin et al. |
| 7,815,602 B2 | 10/2010 | Mann et al. |
| 7,819,843 B2 | 10/2010 | Mann et al. |
| 7,822,455 B2 | 10/2010 | Hoss et al. |
| 7,826,879 B2 | 11/2010 | Hoss et al. |
| 7,828,528 B2 | 11/2010 | Estes et al. |
| 7,831,310 B2 | 11/2010 | Lebel et al. |
| 7,833,196 B2 | 11/2010 | Estes et al. |
| 7,837,647 B2 | 11/2010 | Estes et al. |
| 7,837,651 B2 | 11/2010 | Bishop et al. |
| 7,850,641 B2 | 12/2010 | Lebel et al. |
| 7,860,544 B2 | 12/2010 | Say et al. |
| 7,869,851 B2 | 1/2011 | Hellwig et al. |
| 7,869,853 B1 | 1/2011 | Say et al. |
| 7,875,022 B2 | 1/2011 | Wenger et al. |
| 7,884,729 B2 | 2/2011 | Reggiardo et al. |
| 7,885,699 B2 | 2/2011 | Say et al. |
| 7,887,512 B2 | 2/2011 | Estes et al. |
| 7,890,295 B2 | 2/2011 | Shin et al. |
| 7,892,199 B2 | 2/2011 | Mhatre et al. |
| 7,901,394 B2 | 3/2011 | Ireland et al. |
| 7,912,674 B2 | 3/2011 | Killoren et al. |
| 7,914,450 B2 | 3/2011 | Goode, Jr. et al. |
| 7,914,499 B2 | 3/2011 | Gonnelli et al. |
| 7,920,907 B2 | 4/2011 | McGarraugh et al. |
| 7,933,780 B2 | 4/2011 | De |
| 7,935,076 B2 | 5/2011 | Estes et al. |
| 7,938,797 B2 | 5/2011 | Estes |
| 7,938,803 B2 | 5/2011 | Mernoe et al. |
| 7,941,200 B2 | 5/2011 | Weinert et al. |
| 7,942,844 B2 | 5/2011 | Moberg et al. |
| 7,946,985 B2 | 5/2011 | Mastrototaro et al. |
| 7,951,114 B2 | 5/2011 | Rush et al. |
| 7,959,598 B2 | 6/2011 | Estes |
| 7,963,946 B2 | 6/2011 | Moubayed et al. |
| 7,967,773 B2 | 6/2011 | Amborn et al. |
| 7,972,296 B2 | 7/2011 | Braig et al. |
| 7,976,492 B2 | 7/2011 | Brauker et al. |
| 7,981,034 B2 | 7/2011 | Jennewine et al. |
| 7,981,084 B2 | 7/2011 | Estes et al. |
| 7,981,102 B2 | 7/2011 | Patel et al. |
| 7,983,745 B2 | 7/2011 | Hatlestad et al. |
| 7,983,759 B2 | 7/2011 | Stahmann et al. |
| 7,985,330 B2 | 7/2011 | Wang et al. |
| 7,988,630 B1 | 8/2011 | Osorio et al. |
| 7,988,849 B2 | 8/2011 | Biewer et al. |
| 7,996,158 B2 | 8/2011 | Hayter et al. |
| 8,000,763 B2 | 8/2011 | Mazza et al. |
| 8,005,524 B2 | 8/2011 | Brauker et al. |
| 8,012,119 B2 | 9/2011 | Estes et al. |
| 8,016,783 B2 | 9/2011 | Pastore et al. |
| 8,025,634 B1 | 9/2011 | Moubayed et al. |
| 8,029,443 B2 | 10/2011 | Goodnow |
| 8,029,459 B2 | 10/2011 | Rush et al. |

(56) References Cited

U.S. PATENT DOCUMENTS

| | | |
|---|---|---|
| 8,029,460 B2 | 10/2011 | Rush et al. |
| 8,062,249 B2 | 11/2011 | Wilinska et al. |
| 8,066,665 B2 | 11/2011 | Rush et al. |
| 8,075,527 B2 | 12/2011 | Rush et al. |
| 8,079,983 B2 | 12/2011 | Rush et al. |
| 8,079,984 B2 | 12/2011 | Rush et al. |
| 8,083,718 B2 | 12/2011 | Rush et al. |
| 8,088,098 B2 | 1/2012 | Yodfat et al. |
| 8,090,435 B2 | 1/2012 | Gill et al. |
| 8,093,212 B2 | 1/2012 | Gardner et al. |
| 8,105,268 B2 | 1/2012 | Lebel et al. |
| 8,105,279 B2 | 1/2012 | Mernoe et al. |
| 8,109,921 B2 | 2/2012 | Estes et al. |
| 8,114,350 B1 | 2/2012 | Silver et al. |
| 8,118,770 B2 | 2/2012 | Galley et al. |
| 8,119,593 B2 | 2/2012 | Richardson et al. |
| 8,121,857 B2 | 2/2012 | Galasso et al. |
| 8,127,046 B2 | 2/2012 | Grant et al. |
| 8,129,429 B2 | 3/2012 | Sporn et al. |
| 8,133,197 B2 | 3/2012 | Blomquist et al. |
| 8,140,275 B2 | 3/2012 | Campbell et al. |
| 8,140,312 B2 | 3/2012 | Hayter et al. |
| RE43,316 E | 4/2012 | Brown et al. |
| 8,147,446 B2 | 4/2012 | Yodfat et al. |
| 8,152,789 B2 | 4/2012 | Starkweather et al. |
| 8,170,721 B2 | 5/2012 | Nickerson |
| 8,177,716 B2 | 5/2012 | Say et al. |
| 8,182,445 B2 | 5/2012 | Moubayed et al. |
| 8,187,183 B2 | 5/2012 | Jin et al. |
| 8,192,394 B2 | 6/2012 | Estes et al. |
| 8,192,395 B2 | 6/2012 | Estes et al. |
| 8,202,267 B2 | 6/2012 | Field et al. |
| 8,204,729 B2 | 6/2012 | Sher |
| 8,206,296 B2 | 6/2012 | Jennewine |
| 8,206,350 B2 | 6/2012 | Mann et al. |
| 8,208,984 B2 | 6/2012 | Blomquist et al. |
| 8,211,062 B2 | 7/2012 | Estes et al. |
| 8,219,222 B2 | 7/2012 | Blomquist |
| 8,221,345 B2 | 7/2012 | Blomquist |
| 8,221,385 B2 | 7/2012 | Estes |
| 8,226,558 B2 | 7/2012 | Say et al. |
| 8,226,891 B2 | 7/2012 | Sloan et al. |
| 8,231,562 B2 | 7/2012 | Buck et al. |
| 8,234,126 B1 | 7/2012 | Estes |
| 8,234,128 B2 | 7/2012 | Martucci et al. |
| 8,237,715 B2 | 8/2012 | Buck et al. |
| 8,246,540 B2 | 8/2012 | Ginsberg |
| 8,250,483 B2 | 8/2012 | Blomquist |
| 8,251,904 B2 | 8/2012 | Zivitz et al. |
| 8,251,906 B2 | 8/2012 | Brauker et al. |
| 8,257,259 B2 | 9/2012 | Brauker et al. |
| 8,257,300 B2 | 9/2012 | Budiman et al. |
| 8,260,630 B2 | 9/2012 | Brown |
| 8,262,617 B2 | 9/2012 | Aeschlimann et al. |
| 8,275,438 B2 | 9/2012 | Simpson |
| 8,277,435 B2 | 10/2012 | Estes |
| 8,282,601 B2 | 10/2012 | Mernoe et al. |
| 8,287,454 B2 | 10/2012 | Wolpert et al. |
| 8,287,487 B2 | 10/2012 | Estes |
| 8,287,495 B2 | 10/2012 | Michaud et al. |
| 8,287,514 B2 | 10/2012 | Miller et al. |
| 8,290,562 B2 | 10/2012 | Goode, Jr. et al. |
| 8,298,184 B2 | 10/2012 | Diperna et al. |
| 8,308,680 B1 | 11/2012 | Chawla |
| 8,311,749 B2 | 11/2012 | Brauker et al. |
| 8,323,188 B2 | 12/2012 | Tran |
| 8,326,546 B2 | 12/2012 | Stewart et al. |
| 8,328,754 B2 | 12/2012 | Estes et al. |
| 8,343,092 B2 | 1/2013 | Rush et al. |
| 8,344,847 B2 | 1/2013 | Moberg et al. |
| 8,346,399 B2 | 1/2013 | Blomquist |
| 8,348,885 B2 | 1/2013 | Moberg et al. |
| 8,348,886 B2 | 1/2013 | Kanderian, Jr. et al. |
| 8,348,923 B2 | 1/2013 | Kanderian, Jr. et al. |
| 8,349,319 B2 | 1/2013 | Schuchman et al. |
| 8,353,881 B2 | 1/2013 | Jennewine |
| 8,357,091 B2 | 1/2013 | Say et al. |
| 8,369,919 B2 | 2/2013 | Kamath et al. |
| 8,372,040 B2 | 2/2013 | Huang et al. |
| 8,376,943 B2 | 2/2013 | Kovach et al. |
| 8,377,031 B2 | 2/2013 | Hayter et al. |
| 8,380,273 B2 | 2/2013 | Say et al. |
| 8,409,131 B2 | 4/2013 | Say et al. |
| 8,414,523 B2 | 4/2013 | Blomquist et al. |
| 8,414,532 B2 | 4/2013 | Brandt et al. |
| 8,444,595 B2 | 5/2013 | Brukalo et al. |
| 8,449,523 B2 | 5/2013 | Brukalo et al. |
| 8,449,524 B2 | 5/2013 | Braig et al. |
| 8,451,230 B2 | 5/2013 | Celentano et al. |
| 8,452,953 B2 | 5/2013 | Buck et al. |
| 8,454,510 B2 | 6/2013 | Yodfat et al. |
| 8,454,575 B2 | 6/2013 | Estes et al. |
| 8,454,576 B2 | 6/2013 | Mastrototaro et al. |
| 8,454,581 B2 | 6/2013 | Estes et al. |
| 8,460,231 B2 | 6/2013 | Brauker et al. |
| 8,465,460 B2 | 6/2013 | Yodfat et al. |
| 8,467,980 B2 | 6/2013 | Campbell et al. |
| 8,486,005 B2 | 7/2013 | Yodfat et al. |
| 8,552,880 B2 | 10/2013 | Kopp et al. |
| 8,562,558 B2 | 10/2013 | Kamath et al. |
| 8,573,027 B2 | 11/2013 | Rosinko et al. |
| 8,579,853 B2 | 11/2013 | Reggiardo et al. |
| 8,650,937 B2 | 2/2014 | Brown |
| 8,657,779 B2 | 2/2014 | Blomquist |
| 8,712,748 B2 | 4/2014 | Thukral et al. |
| 8,718,949 B2 | 5/2014 | Blomquist et al. |
| 8,726,266 B2 | 5/2014 | Kiaie et al. |
| 8,775,877 B2 | 7/2014 | McVey et al. |
| 8,801,657 B2 | 8/2014 | Blomquist et al. |
| 8,852,152 B2 | 10/2014 | Tverskoy |
| 8,882,701 B2 | 11/2014 | Debelser et al. |
| 8,936,565 B2 | 1/2015 | Chawla |
| 8,961,465 B2 | 2/2015 | Blomquist |
| 8,985,253 B2 | 3/2015 | Winter et al. |
| 8,986,253 B2 | 3/2015 | Diperna |
| 9,008,803 B2 | 4/2015 | Blomquist |
| 9,037,254 B2 | 5/2015 | John |
| 9,089,305 B2 | 7/2015 | Hovorka |
| 9,114,210 B2 | 8/2015 | Estes |
| 9,364,679 B2 | 6/2016 | John |
| 9,474,856 B2 | 10/2016 | Blomquist |
| 9,483,615 B2 | 11/2016 | Roberts |
| 9,486,171 B2 | 11/2016 | Saint |
| 9,486,578 B2 | 11/2016 | Finan et al. |
| 9,492,608 B2 | 11/2016 | Saint |
| 9,669,160 B2 | 6/2017 | Harris et al. |
| 9,833,177 B2 | 12/2017 | Blomquist |
| 9,867,937 B2 | 1/2018 | Saint et al. |
| 9,867,953 B2 | 1/2018 | Rosinko |
| 9,968,302 B2 | 5/2018 | Fennell |
| 9,968,306 B2 | 5/2018 | Cole |
| 9,968,729 B2 | 5/2018 | Estes |
| 9,974,472 B2 | 5/2018 | Hayter et al. |
| 1,001,655 A1 | 7/2018 | Debelser et al. |
| 1,001,656 A1 | 7/2018 | Saint et al. |
| 1,005,204 A1 | 8/2018 | Blomquist et al. |
| 1,020,704 A1 | 2/2019 | Estes |
| 1,021,354 A1 | 2/2019 | Rosinko |
| 1,035,760 A1 | 7/2019 | Rosinko et al. |
| 2001/0001144 A1 | 5/2001 | Kapp |
| 2001/0027791 A1 | 10/2001 | Wallace et al. |
| 2001/0031944 A1 | 10/2001 | Peterson et al. |
| 2001/0037217 A1 | 11/2001 | Abensour et al. |
| 2001/0041831 A1 | 11/2001 | Starkweather et al. |
| 2002/0002326 A1 | 1/2002 | Causey et al. |
| 2002/0016568 A1 | 2/2002 | Lebel et al. |
| 2002/0065454 A1 | 5/2002 | Lebel et al. |
| 2002/0072932 A1 | 6/2002 | Swamy |
| 2002/0077852 A1 | 6/2002 | Ford et al. |
| 2002/0107476 A1 | 8/2002 | Mann et al. |
| 2002/0143580 A1 | 10/2002 | Bristol et al. |
| 2002/0183693 A1 | 12/2002 | Peterson et al. |
| 2002/0193679 A1 | 12/2002 | Malave et al. |

(56) References Cited

U.S. PATENT DOCUMENTS

| | | | |
|---|---|---|---|
| 2003/0028089 A1* | 2/2003 | Galley | A61B 5/14532 600/365 |
| 2003/0032867 A1 | 2/2003 | Crothall et al. | |
| 2003/0036683 A1 | 2/2003 | Kehr et al. | |
| 2003/0050621 A1* | 3/2003 | Lebel | A61M 5/14276 604/890.1 |
| 2003/0055323 A1* | 3/2003 | Choi | A61B 5/157 600/316 |
| 2003/0060765 A1 | 3/2003 | Campbell et al. | |
| 2003/0065308 A1 | 4/2003 | Lebel et al. | |
| 2003/0088238 A1 | 5/2003 | Poulsen et al. | |
| 2003/0104982 A1 | 6/2003 | Wittmann et al. | |
| 2003/0114836 A1 | 6/2003 | Estes et al. | |
| 2003/0130616 A1* | 7/2003 | Steil | A61B 5/14532 604/66 |
| 2003/0145854 A1 | 8/2003 | Hickle | |
| 2003/0159945 A1 | 8/2003 | Miyazaki et al. | |
| 2003/0160683 A1 | 8/2003 | Blomquist | |
| 2003/0161744 A1 | 8/2003 | Vilks et al. | |
| 2003/0163088 A1 | 8/2003 | Blomquist | |
| 2003/0163090 A1 | 8/2003 | Blomquist et al. | |
| 2003/0163223 A1 | 8/2003 | Blomquist | |
| 2003/0163789 A1 | 8/2003 | Blomquist | |
| 2003/0199854 A1 | 10/2003 | Kovach et al. | |
| 2003/0208113 A1 | 11/2003 | Mault et al. | |
| 2003/0212364 A1 | 11/2003 | Mann et al. | |
| 2003/0212379 A1 | 11/2003 | Bylund et al. | |
| 2003/0236489 A1 | 12/2003 | Jacobson et al. | |
| 2004/0015102 A1 | 1/2004 | Cummings et al. | |
| 2004/0015132 A1 | 1/2004 | Brown | |
| 2004/0054263 A1 | 3/2004 | Moerman et al. | |
| 2004/0068230 A1 | 4/2004 | Estes et al. | |
| 2004/0073095 A1 | 4/2004 | Causey et al. | |
| 2004/0115067 A1 | 6/2004 | Rush et al. | |
| 2004/0122353 A1 | 6/2004 | Shahmirian et al. | |
| 2004/0152622 A1 | 8/2004 | Keith et al. | |
| 2004/0167464 A1 | 8/2004 | Ireland et al. | |
| 2004/0180810 A1 | 9/2004 | Pilarski | |
| 2004/0193025 A1 | 9/2004 | Steil et al. | |
| 2004/0193090 A1 | 9/2004 | Lebel et al. | |
| 2004/0199409 A1 | 10/2004 | Brown | |
| 2004/0220517 A1 | 11/2004 | Starkweather et al. | |
| 2004/0225252 A1 | 11/2004 | Gillespie et al. | |
| 2004/0254434 A1 | 12/2004 | Goodnow et al. | |
| 2005/0017151 A1 | 1/2005 | Battig | |
| 2005/0019755 A1 | 1/2005 | Marchessault et al. | |
| 2005/0021006 A1 | 1/2005 | Tonnies | |
| 2005/0022274 A1* | 1/2005 | Campbell | G06Q 50/22 604/131 |
| 2005/0027182 A1 | 2/2005 | Siddiqui et al. | |
| 2005/0030164 A1 | 2/2005 | Blomquist | |
| 2005/0038332 A1* | 2/2005 | Saidara | A61B 5/0002 600/347 |
| 2005/0049179 A1 | 3/2005 | Davidson et al. | |
| 2005/0050621 A1 | 3/2005 | Thomas | |
| 2005/0065464 A1 | 3/2005 | Talbot et al. | |
| 2005/0065760 A1 | 3/2005 | Murtfeldt et al. | |
| 2005/0081847 A1 | 4/2005 | Lee et al. | |
| 2005/0095063 A1 | 5/2005 | Fathallah et al. | |
| 2005/0137530 A1 | 6/2005 | Campbell et al. | |
| 2005/0143864 A1 | 6/2005 | Blomquist | |
| 2005/0171503 A1* | 8/2005 | Van Den Berghe | A61M 5/142 604/504 |
| 2005/0171513 A1 | 8/2005 | Mann et al. | |
| 2005/0182358 A1 | 8/2005 | Veit et al. | |
| 2005/0192557 A1 | 9/2005 | Brauker et al. | |
| 2005/0197553 A1 | 9/2005 | Cooper | |
| 2005/0197621 A1 | 9/2005 | Poulsen et al. | |
| 2005/0203349 A1 | 9/2005 | Nanikashvili | |
| 2005/0203360 A1 | 9/2005 | Brauker et al. | |
| 2005/0228234 A1 | 10/2005 | Yang | |
| 2005/0272640 A1 | 12/2005 | Doyle, III et al. | |
| 2005/0277872 A1 | 12/2005 | Colby, Jr. et al. | |
| 2005/0277912 A1 | 12/2005 | John | |
| 2006/0001538 A1 | 1/2006 | Kraft et al. | |
| 2006/0001550 A1 | 1/2006 | Mann et al. | |
| 2006/0010098 A1* | 1/2006 | Goodnow | G06F 19/324 |
| 2006/0014670 A1 | 1/2006 | Green et al. | |
| 2006/0031094 A1* | 2/2006 | Cohen | G16H 20/10 705/2 |
| 2006/0047192 A1 | 3/2006 | Hellwig et al. | |
| 2006/0047538 A1 | 3/2006 | Condurso et al. | |
| 2006/0060765 A1 | 3/2006 | Huang | |
| 2006/0080059 A1 | 4/2006 | Stupp et al. | |
| 2006/0085223 A1 | 4/2006 | Anderson et al. | |
| 2006/0093785 A1 | 5/2006 | Hickle | |
| 2006/0094985 A1 | 5/2006 | Aceti et al. | |
| 2006/0122577 A1 | 6/2006 | Poulsen et al. | |
| 2006/0132292 A1 | 6/2006 | Blomquist | |
| 2006/0137695 A1 | 6/2006 | Hellwig et al. | |
| 2006/0167345 A1 | 7/2006 | Vespasiani | |
| 2006/0173406 A1 | 8/2006 | Hayes et al. | |
| 2006/0173444 A1 | 8/2006 | Choy et al. | |
| 2006/0202859 A1 | 9/2006 | Mastrototaro et al. | |
| 2006/0224109 A1 | 10/2006 | Steil et al. | |
| 2006/0253097 A1 | 11/2006 | Braig et al. | |
| 2006/0253296 A1 | 11/2006 | Liisberg et al. | |
| 2006/0264895 A1 | 11/2006 | Flanders | |
| 2006/0271020 A1 | 11/2006 | Huang et al. | |
| 2006/0272652 A1* | 12/2006 | Stocker | G16H 50/50 128/898 |
| 2006/0276771 A1 | 12/2006 | Galley et al. | |
| 2007/0016127 A1 | 1/2007 | Staib et al. | |
| 2007/0016170 A1 | 1/2007 | Kovelman | |
| 2007/0016449 A1 | 1/2007 | Cohen et al. | |
| 2007/0021733 A1 | 1/2007 | Hansen et al. | |
| 2007/0033074 A1 | 2/2007 | Nitzan et al. | |
| 2007/0060796 A1 | 3/2007 | Kim | |
| 2007/0060871 A1 | 3/2007 | Istoc et al. | |
| 2007/0060874 A1 | 3/2007 | Nesbitt et al. | |
| 2007/0066956 A1 | 3/2007 | Finkel | |
| 2007/0073236 A1 | 3/2007 | Mernoe et al. | |
| 2007/0078314 A1* | 4/2007 | Grounsell | A61B 5/14532 600/319 |
| 2007/0083152 A1 | 4/2007 | Williams, Jr. et al. | |
| 2007/0083335 A1 | 4/2007 | Moerman | |
| 2007/0093786 A1 | 4/2007 | Goldsmith et al. | |
| 2007/0100222 A1* | 5/2007 | Mastrototaro | A61B 5/01 600/365 |
| 2007/0106135 A1 | 5/2007 | Sloan et al. | |
| 2007/0112261 A1 | 5/2007 | Enegren et al. | |
| 2007/0112298 A1* | 5/2007 | Mueller, Jr. | A61M 5/14244 604/65 |
| 2007/0112299 A1 | 5/2007 | Smit et al. | |
| 2007/0118405 A1 | 5/2007 | Campbell et al. | |
| 2007/0124002 A1* | 5/2007 | Estes | A61M 5/172 700/20 |
| 2007/0149861 A1 | 6/2007 | Crothall et al. | |
| 2007/0156033 A1 | 7/2007 | Causey, III et al. | |
| 2007/0156092 A1 | 7/2007 | Estes et al. | |
| 2007/0156457 A1 | 7/2007 | Brown | |
| 2007/0167905 A1 | 7/2007 | Estes et al. | |
| 2007/0167912 A1 | 7/2007 | Causey et al. | |
| 2007/0173712 A1 | 7/2007 | Shah et al. | |
| 2007/0173761 A1* | 7/2007 | Kanderian, Jr. | A61B 5/14532 604/131 |
| 2007/0173762 A1 | 7/2007 | Estes et al. | |
| 2007/0179355 A1 | 8/2007 | Rosen | |
| 2007/0179444 A1 | 8/2007 | Causey et al. | |
| 2007/0203454 A1 | 8/2007 | Shermer et al. | |
| 2007/0213657 A1 | 9/2007 | Jennewine et al. | |
| 2007/0233051 A1 | 10/2007 | Hohl et al. | |
| 2007/0245258 A1 | 10/2007 | Ginggen et al. | |
| 2007/0251835 A1 | 11/2007 | Mehta et al. | |
| 2007/0253021 A1 | 11/2007 | Mehta et al. | |
| 2007/0253380 A1 | 11/2007 | Jollota et al. | |
| 2007/0254593 A1 | 11/2007 | Jollota et al. | |
| 2007/0255116 A1 | 11/2007 | Mehta et al. | |
| 2007/0255125 A1 | 11/2007 | Moberg et al. | |
| 2007/0255126 A1 | 11/2007 | Moberg et al. | |
| 2007/0255250 A1 | 11/2007 | Moberg et al. | |
| 2007/0255348 A1 | 11/2007 | Holtzclaw | |
| 2007/0258395 A1 | 11/2007 | Jollota et al. | |

(56) References Cited

U.S. PATENT DOCUMENTS

| | | |
|---|---|---|
| 2007/0287985 A1 | 12/2007 | Estes et al. |
| 2007/0299389 A1 | 12/2007 | Halbert et al. |
| 2008/0004601 A1 | 1/2008 | Jennewine et al. |
| 2008/0017203 A1 | 1/2008 | Fagg et al. |
| 2008/0030369 A1 | 2/2008 | Mann et al. |
| 2008/0033357 A1 | 2/2008 | Mann et al. |
| 2008/0033360 A1 | 2/2008 | Evans et al. |
| 2008/0033361 A1 | 2/2008 | Evans et al. |
| 2008/0045902 A1 | 2/2008 | Estes et al. |
| 2008/0045903 A1 | 2/2008 | Estes et al. |
| 2008/0045904 A1 | 2/2008 | Estes et al. |
| 2008/0045931 A1 | 2/2008 | Estes et al. |
| 2008/0051709 A1 | 2/2008 | Mounce et al. |
| 2008/0051714 A1 | 2/2008 | Moberg et al. |
| 2008/0051716 A1 | 2/2008 | Stutz |
| 2008/0058773 A1 | 3/2008 | John |
| 2008/0065007 A1 | 3/2008 | Peterson et al. |
| 2008/0065016 A1 | 3/2008 | Peterson et al. |
| 2008/0071209 A1 | 3/2008 | Moubayed et al. |
| 2008/0071210 A1 | 3/2008 | Moubayed et al. |
| 2008/0071217 A1 | 3/2008 | Moubayed et al. |
| 2008/0071251 A1 | 3/2008 | Moubayed et al. |
| 2008/0071580 A1 | 3/2008 | Marcus et al. |
| 2008/0076969 A1 | 3/2008 | Kraft et al. |
| 2008/0097289 A1* | 4/2008 | Steil ............... A61M 5/1723 604/67 |
| 2008/0103447 A1 | 5/2008 | Reggiardo et al. |
| 2008/0106431 A1 | 5/2008 | Blomquist |
| 2008/0114299 A1 | 5/2008 | Damgaard-Sorensen et al. |
| 2008/0132844 A1 | 6/2008 | Peterson et al. |
| 2008/0139907 A1 | 6/2008 | Rao et al. |
| 2008/0139910 A1* | 6/2008 | Mastrototaro ......... G16H 40/63 600/365 |
| 2008/0147004 A1 | 6/2008 | Mann et al. |
| 2008/0147041 A1 | 6/2008 | Kristensen |
| 2008/0147042 A1 | 6/2008 | Pettis et al. |
| 2008/0147050 A1 | 6/2008 | Mann et al. |
| 2008/0154513 A1 | 6/2008 | Kovatchev et al. |
| 2008/0156661 A1 | 7/2008 | Cooper et al. |
| 2008/0171697 A1 | 7/2008 | Jacotot et al. |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0177165 A1 | 7/2008 | Blomquist et al. |
| 2008/0183060 A1 | 7/2008 | Steil et al. |
| 2008/0206799 A1 | 8/2008 | Blomquist |
| 2008/0222246 A1 | 9/2008 | Ebling et al. |
| 2008/0228055 A1* | 9/2008 | Sher ................ A61B 5/14532 600/365 |
| 2008/0228056 A1 | 9/2008 | Blomquist et al. |
| 2008/0249470 A1 | 10/2008 | Malave et al. |
| 2008/0255438 A1 | 10/2008 | Saidara et al. |
| 2008/0255517 A1 | 10/2008 | Nair et al. |
| 2008/0264024 A1 | 10/2008 | Baaken |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287922 A1 | 11/2008 | Panduro |
| 2008/0288115 A1 | 11/2008 | Rusnak et al. |
| 2008/0294024 A1 | 11/2008 | Cosentino et al. |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel et al. |
| 2008/0294294 A1* | 11/2008 | Blomquist .......... A61M 5/1723 700/282 |
| 2008/0300534 A1 | 12/2008 | Blomquist |
| 2008/0300572 A1 | 12/2008 | Rankers et al. |
| 2008/0300651 A1 | 12/2008 | Gerber et al. |
| 2008/0306353 A1 | 12/2008 | Douglas et al. |
| 2008/0306434 A1 | 12/2008 | Dobbles et al. |
| 2008/0306444 A1 | 12/2008 | Brister et al. |
| 2008/0312584 A1 | 12/2008 | Montgomery et al. |
| 2008/0312585 A1 | 12/2008 | Brukalo et al. |
| 2009/0005726 A1 | 1/2009 | Jones et al. |
| 2009/0006061 A1 | 1/2009 | Thukral et al. |
| 2009/0006129 A1 | 1/2009 | Thukral et al. |
| 2009/0018779 A1 | 1/2009 | Cohen et al. |
| 2009/0030733 A1 | 1/2009 | Cohen et al. |
| 2009/0036753 A1 | 2/2009 | King |
| 2009/0054475 A1 | 2/2009 | Chen et al. |
| 2009/0054750 A1* | 2/2009 | Jennewine ......... A61B 5/14532 600/316 |
| 2009/0067989 A1 | 3/2009 | Estes et al. |
| 2009/0069745 A1 | 3/2009 | Estes et al. |
| 2009/0069749 A1 | 3/2009 | Miller et al. |
| 2009/0069787 A1 | 3/2009 | Estes et al. |
| 2009/0085768 A1 | 4/2009 | Patel et al. |
| 2009/0088731 A1 | 4/2009 | Campbell et al. |
| 2009/0093756 A1 | 4/2009 | Minaie et al. |
| 2009/0105636 A1 | 4/2009 | Hayter et al. |
| 2009/0105646 A1 | 4/2009 | Hendrixson et al. |
| 2009/0112626 A1 | 4/2009 | Talbot et al. |
| 2009/0118592 A1* | 5/2009 | Klitgaard ............ A61B 5/6849 600/300 |
| 2009/0131860 A1 | 5/2009 | Nielsen |
| 2009/0131861 A1 | 5/2009 | Braig et al. |
| 2009/0143661 A1 | 6/2009 | Taub et al. |
| 2009/0150186 A1 | 6/2009 | Cohen et al. |
| 2009/0150865 A1 | 6/2009 | Young et al. |
| 2009/0156990 A1 | 6/2009 | Wenger et al. |
| 2009/0157003 A1 | 6/2009 | Jones et al. |
| 2009/0163855 A1 | 6/2009 | Shin et al. |
| 2009/0164239 A1 | 6/2009 | Hayter |
| 2009/0171269 A1 | 7/2009 | Jennewine et al. |
| 2009/0177142 A1 | 7/2009 | Blomquist et al. |
| 2009/0177147 A1 | 7/2009 | Blomquist et al. |
| 2009/0177154 A1 | 7/2009 | Blomquist |
| 2009/0177180 A1 | 7/2009 | Rubalcaba, Jr. et al. |
| 2009/0192366 A1 | 7/2009 | Mensinger et al. |
| 2009/0192724 A1 | 7/2009 | Brauker et al. |
| 2009/0192745 A1 | 7/2009 | Kamath et al. |
| 2009/0212966 A1 | 8/2009 | Panduro |
| 2009/0216100 A1 | 8/2009 | Ebner et al. |
| 2009/0221890 A1 | 9/2009 | Saffer et al. |
| 2009/0240193 A1 | 9/2009 | Mensinger et al. |
| 2009/0247931 A1 | 10/2009 | Damgaard-Sorensen |
| 2009/0247982 A1 | 10/2009 | Krulevitch et al. |
| 2009/0254037 A1 | 10/2009 | Bryant, Jr. et al. |
| 2009/0267774 A1 | 10/2009 | Enegren et al. |
| 2009/0267775 A1 | 10/2009 | Enegren et al. |
| 2009/0270705 A1 | 10/2009 | Enegren et al. |
| 2009/0270810 A1 | 10/2009 | Debelser et al. |
| 2009/0275886 A1 | 11/2009 | Blomquist et al. |
| 2009/0275887 A1 | 11/2009 | Estes |
| 2009/0281393 A1 | 11/2009 | Smith |
| 2010/0008795 A1 | 1/2010 | Diperna |
| 2010/0010330 A1 | 1/2010 | Rankers et al. |
| 2010/0030045 A1 | 2/2010 | Gottlieb et al. |
| 2010/0030387 A1 | 2/2010 | Sen |
| 2010/0049164 A1 | 2/2010 | Estes |
| 2010/0056993 A1 | 3/2010 | Chase |
| 2010/0057040 A1 | 3/2010 | Hayter |
| 2010/0057043 A1 | 3/2010 | Kovatchev et al. |
| 2010/0064257 A1 | 3/2010 | Buck et al. |
| 2010/0069730 A1 | 3/2010 | Bergstrom et al. |
| 2010/0081993 A1 | 4/2010 | O'Connor |
| 2010/0094110 A1 | 4/2010 | Heller et al. |
| 2010/0094251 A1 | 4/2010 | Estes |
| 2010/0095229 A1 | 4/2010 | Dixon et al. |
| 2010/0105999 A1 | 4/2010 | Dixon et al. |
| 2010/0114015 A1 | 5/2010 | Kanderian, Jr. et al. |
| 2010/0121169 A1 | 5/2010 | Petisce et al. |
| 2010/0121170 A1 | 5/2010 | Rule |
| 2010/0125241 A1 | 5/2010 | Prud et al. |
| 2010/0130933 A1 | 5/2010 | Holland et al. |
| 2010/0138197 A1 | 6/2010 | Sher |
| 2010/0145173 A1 | 6/2010 | Alferness et al. |
| 2010/0145276 A1 | 6/2010 | Yodfat et al. |
| 2010/0145303 A1 | 6/2010 | Yodfat et al. |

(56) References Cited

U.S. PATENT DOCUMENTS

| | | |
|---|---|---|
| 2010/0156633 A1 | 6/2010 | Buck, Jr. et al. |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0162786 A1 | 7/2010 | Keenan et al. |
| 2010/0168538 A1 | 7/2010 | Keenan et al. |
| 2010/0174266 A1 | 7/2010 | Estes |
| 2010/0174553 A1 | 7/2010 | Kaufman et al. |
| 2010/0179402 A1 | 7/2010 | Goode, Jr. et al. |
| 2010/0185142 A1 | 7/2010 | Kamen et al. |
| 2010/0185152 A1 | 7/2010 | Larsen et al. |
| 2010/0185175 A1 | 7/2010 | Kamen et al. |
| 2010/0192686 A1 | 8/2010 | Kamen et al. |
| 2010/0198034 A1 | 8/2010 | Thomas et al. |
| 2010/0198142 A1 | 8/2010 | Sloan et al. |
| 2010/0202040 A1 | 8/2010 | Morgan |
| 2010/0205001 A1 | 8/2010 | Knudsen et al. |
| 2010/0218132 A1 | 8/2010 | Soni et al. |
| 2010/0222765 A1 | 9/2010 | Blomquist et al. |
| 2010/0228186 A1 | 9/2010 | Estes et al. |
| 2010/0234709 A1 | 9/2010 | Say et al. |
| 2010/0235439 A1 | 9/2010 | Goodnow |
| 2010/0249530 A1 | 9/2010 | Rankers et al. |
| 2010/0249561 A1 | 9/2010 | Patek et al. |
| 2010/0261987 A1 | 10/2010 | Kamath et al. |
| 2010/0262078 A1 | 10/2010 | Blomquist |
| 2010/0262117 A1 | 10/2010 | Magni et al. |
| 2010/0262434 A1 | 10/2010 | Shaya |
| 2010/0274218 A1 | 10/2010 | Yodfat et al. |
| 2010/0274592 A1 | 10/2010 | Nitzan et al. |
| 2010/0274751 A1 | 10/2010 | Blomquist |
| 2010/0277119 A1 | 11/2010 | Montague et al. |
| 2010/0280329 A1 | 11/2010 | Randloev et al. |
| 2010/0280442 A1 | 11/2010 | Shahmirian et al. |
| 2010/0286563 A1 | 11/2010 | Bryer et al. |
| 2010/0286601 A1 | 11/2010 | Yodfat et al. |
| 2010/0286653 A1 | 11/2010 | Kubel et al. |
| 2010/0292634 A1 | 11/2010 | Kircher, Jr. et al. |
| 2010/0295686 A1 | 11/2010 | Sloan et al. |
| 2010/0298681 A1 | 11/2010 | Say et al. |
| 2010/0298685 A1 | 11/2010 | Hayter et al. |
| 2010/0305421 A1 | 12/2010 | Ow-Wing |
| 2010/0305545 A1 | 12/2010 | Kanderian, Jr. et al. |
| 2010/0305965 A1 | 12/2010 | Benjamin et al. |
| 2010/0312085 A1 | 12/2010 | Andrews et al. |
| 2010/0317950 A1 | 12/2010 | Galley et al. |
| 2010/0317951 A1 | 12/2010 | Rutkowski et al. |
| 2010/0324382 A1 | 12/2010 | Cantwell et al. |
| 2010/0324398 A1 | 12/2010 | Tzyy-Ping |
| 2010/0324932 A1 | 12/2010 | Galley et al. |
| 2010/0331651 A1 | 12/2010 | Groll |
| 2011/0004188 A1 | 1/2011 | Shekalim |
| 2011/0006876 A1 | 1/2011 | Moberg et al. |
| 2011/0009725 A1 | 1/2011 | Hill et al. |
| 2011/0009813 A1 | 1/2011 | Rankers |
| 2011/0010105 A1 | 1/2011 | Shah et al. |
| 2011/0015509 A1 | 1/2011 | Peyser |
| 2011/0021898 A1 | 1/2011 | Wei et al. |
| 2011/0022025 A1 | 1/2011 | Savoie et al. |
| 2011/0033833 A1 | 2/2011 | Blomquist et al. |
| 2011/0034792 A1 | 2/2011 | Williams et al. |
| 2011/0040247 A1 | 2/2011 | Mandro et al. |
| 2011/0040251 A1 | 2/2011 | Blomquist et al. |
| 2011/0046051 A1 | 2/2011 | Moerman |
| 2011/0046892 A1 | 2/2011 | Moerman |
| 2011/0047499 A1 | 2/2011 | Mandro et al. |
| 2011/0048938 A1 | 3/2011 | Shah et al. |
| 2011/0048941 A1 | 3/2011 | Shah et al. |
| 2011/0050428 A1 | 3/2011 | Istoc |
| 2011/0053121 A1 | 3/2011 | Heaton |
| 2011/0054281 A1 | 3/2011 | Shah et al. |
| 2011/0054390 A1 | 3/2011 | Searle et al. |
| 2011/0054391 A1 | 3/2011 | Ward et al. |
| 2011/0056264 A1 | 3/2011 | Kaplan et al. |
| 2011/0058485 A1 | 3/2011 | Sloan |
| 2011/0060281 A1 | 3/2011 | Aeschlimann et al. |
| 2011/0071372 A1 | 3/2011 | Sloan et al. |
| 2011/0071464 A1 | 3/2011 | Palerm |
| 2011/0071465 A1 | 3/2011 | Wang et al. |
| 2011/0071765 A1 | 3/2011 | Yodfat et al. |
| 2011/0077481 A1 | 3/2011 | Say et al. |
| 2011/0077963 A1 | 3/2011 | Knudsen et al. |
| 2011/0082439 A1 | 4/2011 | Wenger et al. |
| 2011/0087165 A1 | 4/2011 | Amborn et al. |
| 2011/0092788 A1 | 4/2011 | Long et al. |
| 2011/0092894 A1 | 4/2011 | McGill et al. |
| 2011/0098548 A1 | 4/2011 | Budiman et al. |
| 2011/0098637 A1 | 4/2011 | Hill |
| 2011/0098638 A1 | 4/2011 | Chawla et al. |
| 2011/0098674 A1 | 4/2011 | Vicente et al. |
| 2011/0101995 A1 | 5/2011 | Shah et al. |
| 2011/0105873 A1 | 5/2011 | Feldman et al. |
| 2011/0105955 A1 | 5/2011 | Yudovsky et al. |
| 2011/0106011 A1 | 5/2011 | Cinar et al. |
| 2011/0106049 A1 | 5/2011 | Damiano et al. |
| 2011/0106050 A1 | 5/2011 | Yodfat et al. |
| 2011/0106480 A1 | 5/2011 | Shah et al. |
| 2011/0112504 A1 | 5/2011 | Causey et al. |
| 2011/0112505 A1 | 5/2011 | Starkweather et al. |
| 2011/0112506 A1 | 5/2011 | Starkweather et al. |
| 2011/0118578 A1 | 5/2011 | Timmerman |
| 2011/0118662 A1 | 5/2011 | Mhatre et al. |
| 2011/0118699 A1 | 5/2011 | Yodfat et al. |
| 2011/0124996 A1 | 5/2011 | Reinke et al. |
| 2011/0124999 A1 | 5/2011 | Reggiardo et al. |
| 2011/0125085 A1 | 5/2011 | McGill et al. |
| 2011/0125095 A1 | 5/2011 | Lebel et al. |
| 2011/0126188 A1 | 5/2011 | Bernstein et al. |
| 2011/0130716 A1 | 6/2011 | Estes et al. |
| 2011/0130746 A1 | 6/2011 | Budiman |
| 2011/0133946 A1 | 6/2011 | Kopp et al. |
| 2011/0137239 A1 | 6/2011 | Debelser et al. |
| 2011/0144586 A1 | 6/2011 | Michaud et al. |
| 2011/0144616 A1 | 6/2011 | Michaud et al. |
| 2011/0152770 A1 | 6/2011 | Diperna et al. |
| 2011/0152824 A1 | 6/2011 | Diperna et al. |
| 2011/0160654 A1 | 6/2011 | Hanson et al. |
| 2011/0160695 A1 | 6/2011 | Sigrist et al. |
| 2011/0163881 A1 | 7/2011 | Halff et al. |
| 2011/0166544 A1 | 7/2011 | Verhoef et al. |
| 2011/0166875 A1 | 7/2011 | Hayter et al. |
| 2011/0172744 A1 | 7/2011 | Davis et al. |
| 2011/0178461 A1 | 7/2011 | Chong et al. |
| 2011/0178462 A1 | 7/2011 | Moberg et al. |
| 2011/0178717 A1 | 7/2011 | Goodnow et al. |
| 2011/0184264 A1 | 7/2011 | Galasso et al. |
| 2011/0184342 A1 | 7/2011 | Pesach et al. |
| 2011/0190614 A1 | 8/2011 | Brister et al. |
| 2011/0190701 A1 | 8/2011 | Remde et al. |
| 2011/0193704 A1 | 8/2011 | Harper et al. |
| 2011/0196213 A1 | 8/2011 | Thukral et al. |
| 2011/0202040 A1 | 8/2011 | Remde et al. |
| 2011/0205065 A1 | 8/2011 | Strachan et al. |
| 2011/0208155 A1 | 8/2011 | Palerm et al. |
| 2011/0213225 A1 | 9/2011 | Bernstein et al. |
| 2011/0213306 A1 | 9/2011 | Hanson et al. |
| 2011/0256024 A1 | 10/2011 | Cole et al. |
| 2011/0257625 A1 | 10/2011 | Jasperson et al. |
| 2011/0257627 A1 | 10/2011 | Hovorka |
| 2011/0257895 A1 | 10/2011 | Brauker et al. |
| 2011/0266999 A1 | 11/2011 | Yodfat et al. |
| 2012/0013625 A1 | 1/2012 | Blomquist et al. |
| 2012/0013802 A1 | 1/2012 | Blomquist et al. |
| 2012/0029433 A1 | 2/2012 | Michaud et al. |
| 2012/0029941 A1 | 2/2012 | Malave et al. |
| 2012/0030610 A1 | 2/2012 | Diperna et al. |
| 2012/0041415 A1 | 2/2012 | Estes et al. |
| 2012/0053522 A1 | 3/2012 | Yodfat et al. |
| 2012/0059353 A1 | 3/2012 | Kovatchev et al. |
| 2012/0059673 A1 | 3/2012 | Cohen et al. |
| 2012/0095315 A1 | 4/2012 | Tenbarge et al. |
| 2012/0109100 A1 | 5/2012 | Estes et al. |
| 2012/0123230 A1 | 5/2012 | Brown et al. |
| 2012/0163481 A1 | 6/2012 | Ebner et al. |

(56) References Cited

U.S. PATENT DOCUMENTS

| | | |
|---|---|---|
| 2012/0185267 A1 | 7/2012 | Kamen et al. |
| 2012/0191061 A1 | 7/2012 | Yodfat et al. |
| 2012/0191063 A1 | 7/2012 | Brauker et al. |
| 2012/0203178 A1 | 8/2012 | Tverskoy |
| 2012/0226124 A1 | 9/2012 | Blomquist |
| 2012/0232484 A1 | 9/2012 | Blomquist |
| 2012/0232485 A1 | 9/2012 | Blomquist |
| 2012/0232520 A1 | 9/2012 | Sloan et al. |
| 2012/0232521 A1 | 9/2012 | Blomquist |
| 2012/0238852 A1 | 9/2012 | Brauker et al. |
| 2012/0238854 A1 | 9/2012 | Blomquist et al. |
| 2012/0239362 A1 | 9/2012 | Blomquist |
| 2012/0245524 A1 | 9/2012 | Estes et al. |
| 2012/0265722 A1 | 10/2012 | Blomquist |
| 2012/0296269 A1 | 11/2012 | Blomquist |
| 2012/0302991 A1 | 11/2012 | Blomquist |
| 2012/0330227 A1 | 12/2012 | Budiman et al. |
| 2013/0012917 A1 | 1/2013 | Miller et al. |
| 2013/0046281 A1 | 2/2013 | Javitt |
| 2013/0053816 A1 | 2/2013 | Diperna et al. |
| 2013/0131630 A1 | 5/2013 | Blomquist |
| 2013/0324824 A1 | 12/2013 | Kamath et al. |
| 2013/0324928 A1 | 12/2013 | Kruse |
| 2013/0331790 A1 | 12/2013 | Brown et al. |
| 2013/0345625 A1 | 12/2013 | Causey, III et al. |
| 2013/0345663 A1 | 12/2013 | Agrawal et al. |
| 2014/0005633 A1 | 1/2014 | Finan |
| 2014/0012511 A1 | 1/2014 | Mensinger et al. |
| 2014/0019396 A1 | 1/2014 | Carlsgaard et al. |
| 2014/0054883 A1 | 2/2014 | Lanigan et al. |
| 2014/0066890 A1 | 3/2014 | Sloan et al. |
| 2014/0074059 A1 | 3/2014 | Howell et al. |
| 2014/0137641 A1 | 5/2014 | Brown |
| 2014/0171772 A1 | 6/2014 | Blomquist |
| 2014/0273042 A1 | 9/2014 | Saint |
| 2014/0275419 A1 | 9/2014 | Ward et al. |
| 2014/0276419 A1 | 9/2014 | Rosinko et al. |
| 2014/0276420 A1 | 9/2014 | Rosinko |
| 2014/0276531 A1 | 9/2014 | Walsh |
| 2014/0276553 A1 | 9/2014 | Rosinko et al. |
| 2014/0276556 A1 | 9/2014 | Saint et al. |
| 2014/0276570 A1 | 9/2014 | Saint |
| 2014/0276574 A1 | 9/2014 | Saint |
| 2014/0350371 A1 | 11/2014 | Blomquist et al. |
| 2014/0374275 A1 | 12/2014 | Morales |
| 2014/0378898 A1 | 12/2014 | Rosinko |
| 2015/0045770 A1 | 2/2015 | Debelser et al. |
| 2015/0073337 A1 | 3/2015 | Saint et al. |
| 2015/0157793 A1 | 6/2015 | Kovelman |
| 2015/0174320 A1 | 6/2015 | Grant et al. |
| 2015/0182693 A1 | 7/2015 | Rosinko |
| 2015/0182695 A1 | 7/2015 | Rosinko |
| 2015/0217044 A1 | 8/2015 | Blomquist |
| 2015/0273147 A1 | 10/2015 | Duke et al. |
| 2015/0314062 A1 | 11/2015 | Blomquist et al. |
| 2016/0030669 A1 | 2/2016 | Harris et al. |
| 2016/0082188 A1 | 3/2016 | Blomquist et al. |
| 2016/0199571 A1 | 7/2016 | Rosinko et al. |
| 2016/0228041 A1 | 8/2016 | Heller et al. |
| 2017/0000943 A1 | 1/2017 | Blomquist et al. |
| 2017/0043085 A1 | 2/2017 | Rosinko |
| 2017/0182248 A1 | 6/2017 | Rosinko |
| 2018/0092578 A1 | 4/2018 | Blomquist |
| 2018/0110921 A1 | 4/2018 | Saint et al. |
| 2018/0133397 A1 | 5/2018 | Estes |
| 2018/0137252 A1 | 5/2018 | Mairs et al. |
| 2018/0137938 A1 | 5/2018 | Vaddiraju et al. |
| 2018/0161498 A1 | 6/2018 | Estes |
| 2018/0193573 A1 | 7/2018 | Rosinko |
| 2018/0304010 A1 | 10/2018 | Debelser et al. |
| 2019/0175823 A1 | 6/2019 | Rosinko |

FOREIGN PATENT DOCUMENTS

| | | |
|---|---|---|
| DE | 4407005 C1 | 3/1995 |
| DE | 19819407 A1 | 11/1999 |
| DE | 10121317 A1 | 11/2002 |
| DE | 10352456 A1 | 7/2005 |
| EP | 1102194 A2 | 5/2001 |
| EP | 1571582 A2 | 9/2005 |
| EP | 1500029 B1 | 4/2007 |
| JP | 2006034323 A | 2/2006 |
| JP | 2010503515 A | 2/2010 |
| WO | WO-0045696 A1 | 8/2000 |
| WO | WO-0074753 A1 | 12/2000 |
| WO | WO-0152727 A1 | 7/2001 |
| WO | WO-02062212 A2 | 8/2002 |
| WO | WO-03082091 A2 | 10/2003 |
| WO | WO-2005046559 A2 | 5/2005 |
| WO | WO-2006061169 A1 | 6/2006 |
| WO | WO-2006127841 A2 | 11/2006 |
| WO | WO-2007000425 A2 | 1/2007 |
| WO | WO-2007056592 A2 | 5/2007 |
| WO | WO-2007089537 A1 | 8/2007 |
| WO | WO-2007149533 A2 | 12/2007 |
| WO | WO-2008036658 A2 | 3/2008 |
| WO | WO-2008048556 A2 | 4/2008 |
| WO | WO-2008048582 A1 | 4/2008 |
| WO | WO-2008048583 A1 | 4/2008 |
| WO | WO-2008048584 A1 | 4/2008 |
| WO | WO-2008048585 A1 | 4/2008 |
| WO | WO-2008048586 A1 | 4/2008 |
| WO | WO-2008048587 A1 | 4/2008 |
| WO | WO-2008064254 A2 | 5/2008 |
| WO | WO-2008091320 A2 | 7/2008 |
| WO | WO-2008103175 A1 | 8/2008 |
| WO | WO-2008112078 A2 | 9/2008 |
| WO | WO-2008112078 A3 | 10/2008 |
| WO | WO-2008144693 A1 | 11/2008 |
| WO | WO-2008144695 A1 | 11/2008 |
| WO | WO-2008144697 A1 | 11/2008 |
| WO | WO-2008144698 A1 | 11/2008 |
| WO | WO-2008153689 A1 | 12/2008 |
| WO | WO-2008153819 A1 | 12/2008 |
| WO | WO-2009016636 A2 | 2/2009 |
| WO | WO-2009032399 A1 | 3/2009 |
| WO | WO-2009032400 A1 | 3/2009 |
| WO | WO-2009035759 A1 | 3/2009 |
| WO | WO-2009088983 A2 | 7/2009 |
| WO | WO-2009089028 A2 | 7/2009 |
| WO | WO-2009089029 A2 | 7/2009 |
| WO | WO-2010111505 A2 | 9/2010 |
| WO | WO-2011014704 A2 | 2/2011 |
| WO | WO-2011068648 A2 | 6/2011 |
| WO | WO-2013016363 A2 | 1/2013 |
| WO | WO-2013184896 A1 | 12/2013 |
| WO | WO-2018085600 A1 | 5/2018 |

OTHER PUBLICATIONS

"Compare Insulin Pump for Diabetes," Printed from www.diabetesnet.com/diabetes-technology/insulin-pump-models.php, Jun. 18, 2009, 4 pages.

Application and File History for U.S. Appl. No. 11/753,420, filed May 24, 2007, inventor Blomquist.

Application and File History for U.S. Appl. No. 12/774,991, filed May 6, 2010, inventor Blomquist.

Application and File History for U.S. Appl. No. 13/530,404, filed Jun. 22, 2012, inventor Blomquist.

Application and File History for U.S. Appl. No. 13/800,453, filed Mar. 13, 2013, inventors Rosinko, et al.

Application and File History for U.S. Appl. No. 14/187,414, filed Feb. 24, 2014, inventor Blomquist.

Application and File History for U.S. Appl. No. 15/830,415, filed Dec. 4, 2017, inventor Blomquist.

Application and File History for U.S. Appl. No. 14/962,635, filed Dec. 8, 2015, inventors Blomquist, et al.

Application and File History for U.S. Appl. No. 15/266,468, filed Sep. 15, 2016, inventor Blomquist, et al.

(56) References Cited

OTHER PUBLICATIONS

Application for U.S. Appl. No. 11/685,617, filed Mar. 13, 2007, inventor Blomquist, et al.
Bott, et al., "Impact of Smoking on the Metabolic Action of Subcutaneous Regular Insulin in Type 2 Diabetic Patients," Horm. Metab. Res., vol. 37, 2005, pp. 445-449.
Chase, et at., "The Use of Insulin Pumps With Meal Bolus Alarms in Children With Type 1 Diabetes to Improve Glycemic Control," Diabetes Carem, vol. 29, No. 5, May 2006, pp. 1012-1015.
Diamant B, "Subcutaneous Absorption of Insulin in Insulin-- Dependent Diavetic patients. Influence of Species Physico- Chemical properties of Insulin and Physiological factors," Danish Medical Bulletin, Hildebrandt, Aug. 1991, 10 pages.
Extended European Search Report for Application No. 14775822.1, dated Jan. 4, 2019, 4 pages.
Extended European Search Report for Application No. 14775822.1, dated Nov. 21, 2016, 9 pages.
International Preliminary Report on Patentability for Application No. PCT/US2008/002536, dated Sep. 15, 2009, 9 pages.
International Search Report and Written Opinion for PCT Application No. PCT/US2008/002536 dated Sep. 4, 2008, 12 pages.
International Search Report and Written Opinion for PCT Application No. PCT/US2008/006449 dated Oct. 10, 2008, 17 pages.
International Search Report and Written Opinion for PCT Application No. PCT/US2008/006801 dated Oct. 30, 2008, 17 pages.
International Search Report and Written Opinion for PCT Application No. PCT/US2014/021109 dated Jun. 5, 2014, 13 pages.
Lehmann, et al., "Combining rule-based reasoning and mathematical modeling in diabetes care," Artificial Intelligence in Medicine, vol. 6, 1994, pp. 137-160.
Office Action dated Apr. 4, 2018 for European Application No. 14775822.1, 4 pages.
Office Action dated May 25, 2010 for European Application No. 08779626.4, 7 pages.
Office Action dated Apr. 7, 2010 for European Application No. 08767934.6, 3 pages.
Plougmann, et al., " DiasNet—a diabetes advisory system for communication and education via the internet," International Journal of Medical Informatics, vol. 26, 2001, pp. 319-330.
Puckett, et al., "A model for multiple subcutaneous insulin injections developed from individual diabetic patient data," vol. 269, 1995, p. E1115-E1124.
Smith Medical MD Inc., "Deltec Cozmo, Personalized Insulin Pump, Starting Guide," http://web.archive.org/web/20041207133223/ http://www.cozmore.com/Library/-upload/starting.sub.--guide.sub.-- 032004.pdf, XP002497833, Dec. 7, 2004, pp. 1-83.
Stapel E., "Converting Between Decimals, Fractions, and Percents," Purplemath, 2006, 9 pages, Available at http://www.purplemath. com/modules/percents2.htm, 2006.
Trajanoski, et al., "Pharmacokinetic Model for the Absorption of Subcutaneously Injected Soluble Insulin and Monomeric Insulin Analogues," Biomedizinische Technik, vol. 38, No. 9. Sep. 1, 1993, 8 pages.
Wach, et al., "Numerical Approximation of Mathematical Model for Absorption of Subcutaneously Injected Insulin," Med & Biol. Eng & comput., vol. 33, 1995, pp. 18-23.
Walsh J., et al., "Pumping Insulin: Everything you need for Success on a Smart insulin Pump," Torrey Pines Press, San Diego, ISBN 1-884804-86-1, 2006, 3 pages.
Walsh J., et al., "Select & Test Your Correction Factor," Pumping Insulin, Fourth Edition, Chapter 13, 2006, 10 Pages.
Walsh J., et al., "Select & Test Your Basal Rates," Pumping Insulin, Fourth Edition, Chapter 2006, 30 pages.
Walsh J., et al., "Select and Test Your Carb Factor," Pumping Insulin, Fourth Edition, Chapter 2006, 32 pages.
Walsh, et al., "Diabetes Technology-Concept 1: Super Bolus," available at Diabetes Technology-Concept 1: Super Bolus available at http://www.diabetesnet.com/diabetes.sub.--technology/super.sub.-- bolus.ph-p>, Sep. 17, 2007, 3 pages.
Wikipedia.com, "Wikipedia's definition for "basal rate"," printed from wikipedia.com on Jun. 12, 2009, 1 page.
Wilinska, et al., "Insulin Kinetics in Type-1 Diabetes: Continuous and Bolus Delivery of Rapid Acting Insulin," IEEE Transactions on Biomedical Engineering, vol. 52, No. 1, Jan. 2005, pp. 3-12.

\* cited by examiner

EXPERT SYSTEM FOR INSULIN PUMP THERAPY

RELATED APPLICATIONS

This application is a continuation of application Ser. No. 14/962,535 filed Dec. 8, 2015, which in turn is a continuation of application Ser. No. 14/684,495 filed Apr. 13, 2015, now U.S. Pat. No. 9,474,856 issued Oct. 25, 2016, which in turn is a continuation of application Ser. No. 13/530,404 filed Jun. 22, 2012, now U.S. Pat. No. 9,008,803 issued Apr. 14, 2015, which in turn is a continuation of application Ser. No. 12/774,991 filed May 6, 2010, now U.S. Pat. No. 8,219,222 issued Jul. 10, 2012, which in turn is a continuation application Ser. No. 11/753,420 filed May 24, 2007, now U.S. Pat. No. 7,751,907 issued Jul. 6, 2010, each of which is hereby fully incorporated herein by reference.

TECHNICAL FIELD

The field generally relates to patient insulin management devices and, in particular, but not by way of limitation, to systems, devices and methods for managing insulin therapy.

BACKGROUND

People who suffer from diabetes require insulin to keep their blood glucose level as close as possible to normal levels. It is essential for people with diabetes to manage their blood glucose level to within a normal range. Complications from diabetes can include heart disease (cardiovascular disease), blindness (retinopathy), nerve damage (neuropathy), and kidney damage (nephropathy). Insulin is a hormone that reduces the level of blood glucose in the body. Normally, insulin is produced by beta cells in the pancreas. In non-diabetic people, the beta cells release insulin to satisfy two types of insulin needs. The first type is a low-level of background insulin that is released throughout the day. The second type is a quick release of a higher-level of insulin in response to eating. Insulin therapy replaces or supplements insulin produced by the pancreas.

Conventional insulin therapy typically involves one or two injections a day. The low number of injections has the disadvantage of allowing larger variations in a person's insulin levels. Some people with diabetes manage their blood glucose level with multiple daily injections (MDI). MDI may involve more than three injections a day and four or more blood glucose tests a day. MDI offers better control than conventional therapy. However, insulin injections are inconvenient and require a diabetic person to track the insulin doses, the amount of carbohydrates eaten, and their blood glucose levels among other information critical to control.

It is important for a diabetic person to be treated with the proper amount of insulin. As discussed previously, high blood sugar can lead to serious complications. Conversely, a person with low blood sugar can develop hypoglycemia. Ideally, insulin therapy mimics the way the body works. An insulin pump is one way to mimic the body's insulin production. An insulin pump can provide a background or basal infusion of insulin throughout the day and provide a quick release or bolus of insulin when carbohydrates are eaten. If a person develops high blood sugar, a correction bolus can be delivered by the pump to correct it. While insulin pumps improve convenience and flexibility for a diabetic person, they can be sophisticated devices. Some insulin pumps can be difficult to program. Proper use of an insulin pump requires a user to go through a learning curve to properly treat their diabetes using the insulin pump.

SUMMARY

This document discusses, among other things, devices and methods for managing insulin therapy. A device example includes a controller. The controller includes an input/output (I/O) module and a rule module. The I/O module is configured to present a question for a patient when communicatively coupled to a user interface and receive patient information in response to the question via the user interface. The rule module is configured to apply a rule to the patient information and generate a suggested insulin pump setting from application of the rule.

A method example includes presenting a question for a diabetic patient using a device, receiving patient information into the device in response to the question, applying a rule to the patient information, and generating a suggested insulin pump setting from application of the rule.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, such that "A or B" includes "A but not B,"

"B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1A:
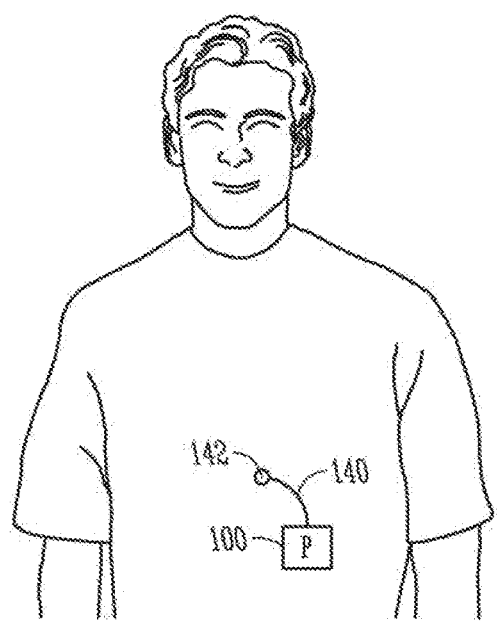
FIGS. 1A and 1B illustrate portions of a device that includes an insulin pump.
Figure 1B:
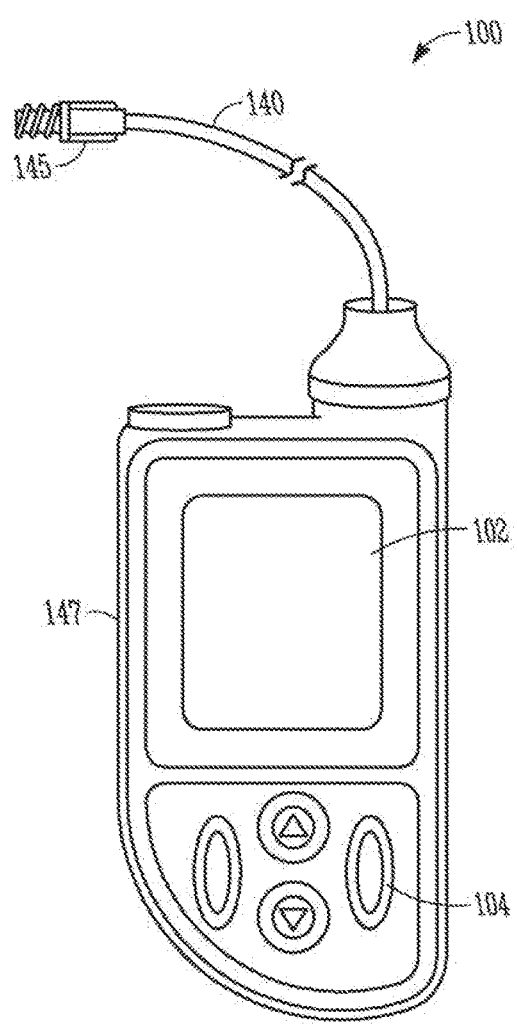

FIGS. 1A and 1B illustrate portions of a device 100 that includes an insulin pump. The device 100 includes a cassette or cartridge of insulin. The cartridge is connectable to infusion tubing 140 connectable to a patient such as by a Luer lock 145 or infusion set 142. The device 100 includes a display 102 and a user interface that may include the display 102 and include one or more keys 104. Because proper use of an insulin pump requires a user to go through a learning curve to properly treat their diabetes using the pump, it is desirable for a pump to provide assistance to the user, whether the user is a diabetic patient, a caregiver, or a clinician. An expert system provides assistance or coaching to the user to effectively treat their diabetes using the insulin pump device.

Figure 2:
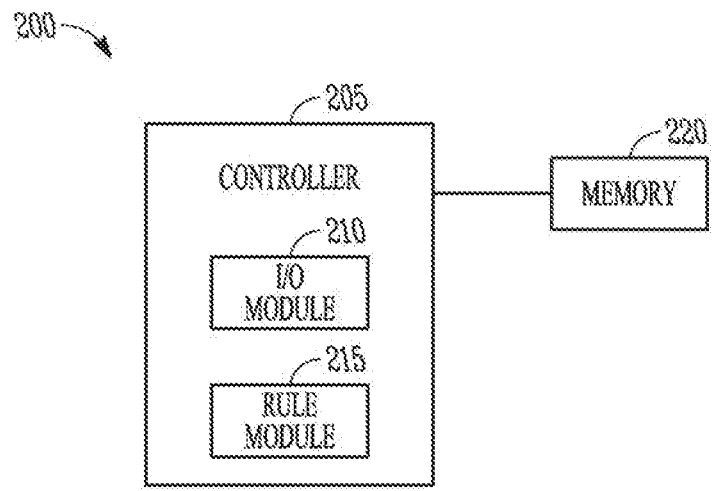
FIG. 2 is a block diagram of an example of portions of a device to provide assistance in maintaining and adjusting a patient's insulin pump therapy.

FIG. 2 is a block diagram of an example of portions of a device 200 to provide assistance in maintaining and adjusting a patient's insulin pump therapy. The device 200 includes a controller 205. The controller 205 can be implemented using hardware circuits, firmware, software or any combination of hardware, firmware and software. Examples, include a microcontroller, a logical state machine, and a processor such as a microprocessor, application specific integrated circuit (ASIC), or other type of processor. The controller 205 is configured to perform or execute a function or functions. Such functions correspond to modules, which are software, hardware, firmware or any combination thereof. Multiple functions may be performed in one or more modules. In some examples, software or firmware is provided on a computer readable medium. The computer readable includes instructions therein, which when processed (such as by the controller 205 for example) results in a device performing the functions described herein. Examples of a computer readable medium include a compact disc (CD), memory stick, or remote storage accessible via a communication network such as the internet or a cell phone network.

The controller 205 includes an input-output (I/O) module 210. The I/O module 210 presents a question for a patient when the I/O module 210 is communicatively coupled to a user interface. The user interface may include one or more pushbuttons or a keypad. The user interface may include a display to visually present instructions and/or the question to the user. The user of the device 200 may be a clinician or a diabetic patient. The display may include a touch-screen. The user interface may include a speaker to present instructions and questions audibly. A speaker may be desirable when the user has difficulty in reading a display.

The I/O module 210 receives patient information in response to the question via the user interface. In some examples, the question and response is included in a series of questions and responses that are part of a patient interview by the device 200. A patient interview may cover a broad range of information. In some examples, the patient information may include patient health information such as a patient health status or whether the patient has any other health-related conditions. The health information also may include whether information concerning any drugs or medications the patient may be taking. Some drugs may cause a person to need more insulin, or the patient may be taking a drug to slow down the absorption of food.

The patient information may include patient lifestyle information. The lifestyle information may include whether a patient tends to eat high glycemic index foods, drinks alcohol, smokes, eats a bedtime snack, a health status of the patient, whether the patient is typically under stress, whether the patient tends to be active, and the amount time the patient spends exercising, for example. The patient information may include patient demographic information. The demographic information may include a patient's weight, age, and gender for example.

In some examples, the patient information may be stored in a memory 220 communicatively coupled to the controller 205. The information may be stored in response to the questions or may be pre-stored in the device 200. The controller 205 includes a rule module 215. The rule module 215 applies a rule to the patient information and generates a suggested insulin pump setting from application of the rule. In some embodiments, the rule includes a decision tree. A decision tree may be implemented with a series of IF-Then logic statements. The controller 205 traverses the decision tree using the patient information. In some embodiments, the rule module 215 may include a look-up table stored in the memory 220. The look-up table may have entries that include one or more insulin pump settings. The table may include multiple dimensions to take into account multiple factors, responses, or other information.

An example of an insulin pump setting is a basal rate. Basal rate refers to a type of twenty-four hour background infusion of insulin by an insulin pump that mimics the continuous background release of insulin from a normal pancreas. It is the rate of insulin delivery the patient normally needs independent of the consumption of meals. The basal rate is typically specified in insulin units per hour (u/hr). The patient information may include a total daily dose (TDD) of insulin, or the rule module may determine a TDD from patient information including the type of diabetes of the patient and the patient's weight, age, and level of fitness. The rule included in the rule module 215 may determine that the amount of daily basal insulin according to a percentage of TDD, such as 40%, 50%, or 60% for example. The percentage applied by the rule may be customized according to the preferences of a clinician. The TDD is then divided by 24 to obtain an average hourly basal rate. For example, if a patient's TDD is determined to be 40 units of insulin, and 50% of the TDD is used for basal delivery, the rule module 215 determines that the average basal rate is 20 units/24 hours or 0.83 u/hr.

Many insulin pump users may use three or more different basal rates during the course of a day. Basal rates can be adjusted to change delivery every few minutes (e.g., 20-30 minutes) by increments as small as 0.05 u/hr to better track changes in demand, such as from an increase typically needed before dawn or a decrease needed during long active periods. The device 200 provides assistance in determining one or more basal rates for the patient. For example, the rule may be a look-up table that includes one or more basal rates indexed by an activity level of the patient. The rule determines a lower basal rate during an increased activity level of the patient. In another example, the rule may increase a basal rate during times when the patient takes a drug that causes the patient to need more insulin. In yet another example, the rule may decrease a basal rate or a segment of a basal rate pattern if the patient is taking a drug to delay the digestion of food.

Another example of an insulin pump setting is a correction factor. A correction factor refers to the amount in drop in blood sugar, or blood glucose, for one unit of insulin. It is measured in milligrams per deciliter (mg/dl) per unit in the U.S. and in millimoles (mmol) per unit in other countries. An insulin pump may use the correction factor to automatically determine a bolus amount required for a high reading or a reduction in a meal bolus for a below-target reading. The insulin pump may also use the correction factor to calculate the amount of carbohydrates a patient should eat to bring low blood sugar up to a target blood sugar level. An appropriate correction factor brings a high blood glucose reading down using an automatically determined correction bolus without a risk of going low.

The rule module 215 may include a rule such as the "1800 rule" in setting the correction factor. For example, if a person's TDD is 40 units of insulin, the correction factor would be 1800/40, or 45 mg/dl per unit. (The 1800 rule corresponds to a "100 rule" if mmol are used.) The rule module 215 may also take into account factors such as a person's age, weight, and activity level when setting the correction factor. Other rules include the 1700 rule (94 rule if mmol) and the 1500 rule (83 rule if mmol). For example, under the 1700 rule the correction factor would be 1700/40 or 42.5 mg/dl. A clinician may prefer one rule over another based on experience including rules that are not based on TDD. The rule to determine the correction factor may be customized according to the preferences of the clinician.

Another example of an insulin pump setting is a carbohydrate ratio. A carbohydrate ratio refers to the amount of carbohydrates covered by a unit of insulin. It is sometimes referred to as a carbohydrate factor, or carb factor, and is typically specified as grams of carbohydrates per unit of insulin. An insulin pump device may use the carbohydrate ratio to automatically determine a carbohydrate insulin bolus amount required to match a number of carbohydrates ingested by the patient, or at least to keep post-meal blood glucose within a range that is healthy for a patient. For example, the patient may plan to eat seventy grams of carbohydrates. If the carbohydrate ratio is ten grams of carbohydrates per unit of insulin, the insulin pump may determine that seven units of insulin are required to cover the carbohydrates.

The rule module 215 may include a formula such as the "500 rule" in setting the carbohydrate ratio. For example, if a person's TDD is 40 units of insulin, the carbohydrate ratio would be 500/40 or about 13 grams per unit of insulin. The rule module 215 may also take into account factors such as a person's age, weight, and activity level when setting the carbohydrate ratio. Other formulas include the 550 rule and the 600 rule. For example, under the 600 rule the carbohydrate ratio would be 600/40 or 15 grams per unit of insulin. As discussed above, the larger the carbohydrate ratio, the smaller a carbohydrate bolus becomes. Because a clinician may prefer one rule over another based on experience; including rules that are not based on TDD, the rule to determine the correction factor may be customized according to the preferences of the clinician.

According to some examples, the memory 220 may store parameters associated with an insulin pump initial setup. The rule module 215 applies a rule to match the insulin pump parameters to at least one of patient health information, patient lifestyle information, and patient demographic information to generate a suggested insulin pump initial setup. The rule module 215 may apply the rule to the patient information to determine at least one of an initial correction factor, an initial carbohydrate ratio, and one or more initial basal rate patterns or profiles. For example, as part of the device interview a patient may enter those periods when the patient regularly exercises into the device 200. The rule may generate different basal rates before, during, or after the exercise periods. In another example, the patient enter the fact that she is pregnant or trying to get pregnant into the device 200. The rule may suggest more aggressive correction bolus targets. In a further example, based on the demographic data the rule may determine different insulin pump initial setups for children, teens, adult females, adult males, and seniors. The demographic information would initially setup parameters including basal rates, carbohydrate bolus limits, insulin pump feature lockouts and enables.

Figure 3:
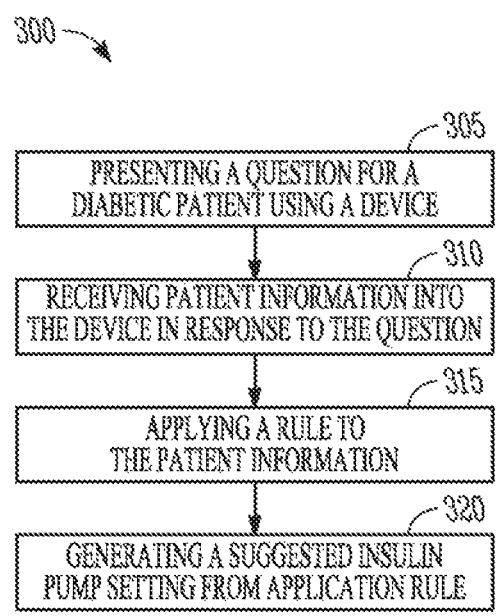
FIG. 3 shows a flow diagram of a method to provide assistance in maintaining and adjusting a patient's insulin pump therapy.

FIG. 3 shows a flow diagram of a method to provide assistance in maintaining and adjusting a patient's insulin pump therapy. At block 305, a question is presented for a diabetic patient using a device. At block 310, patient information is received into the device in response to the question. At block 315, a rule is applied to the patient information. At block 320, a suggested insulin pump setting is generated from application of the rule.

Figure 4:
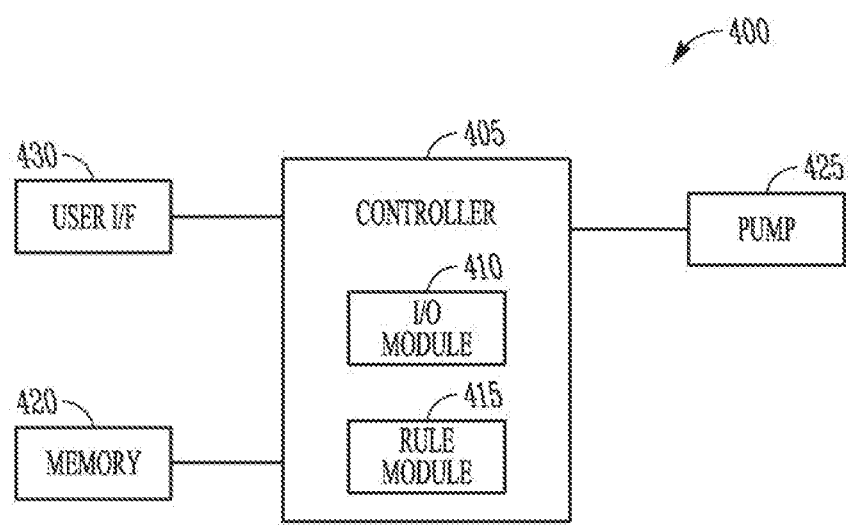
FIG. 4 is a block diagram of another example of portions of a device to provide assistance in maintaining and adjusting a patient's insulin pump therapy.

FIG. 4 is a block diagram of another example of portions of a device 400 to provide assistance in maintaining and adjusting a patient's insulin pump therapy. The device 400 includes an insulin pump 425 or pump mechanism to deliver insulin to a patient, such as a positive displacement pump for example. The device 400 also includes a controller 405 communicatively coupled to a memory 420. The controller 405 includes an I/O module 410 and a rule module 415. The memory 420 may store parameters associated with insulin pump therapy. The rule module 415 applies a rule to generate a suggested insulin pump initial setup.

The device 400 includes a user interface 430 communicatively coupled to the I/O module 410. In some examples, the user interface 430 includes a display and the I/O module 410 presents one or more suggested insulin pump settings to the user via the user interface 430. The I/O module additionally presents a request to the user for confirmation of the insulin pump setting. After a request is received, the setting or settings are adopted or activated by the device 400, such as by moving the settings from the memory 420 to operating registers for example.

Figure 5:
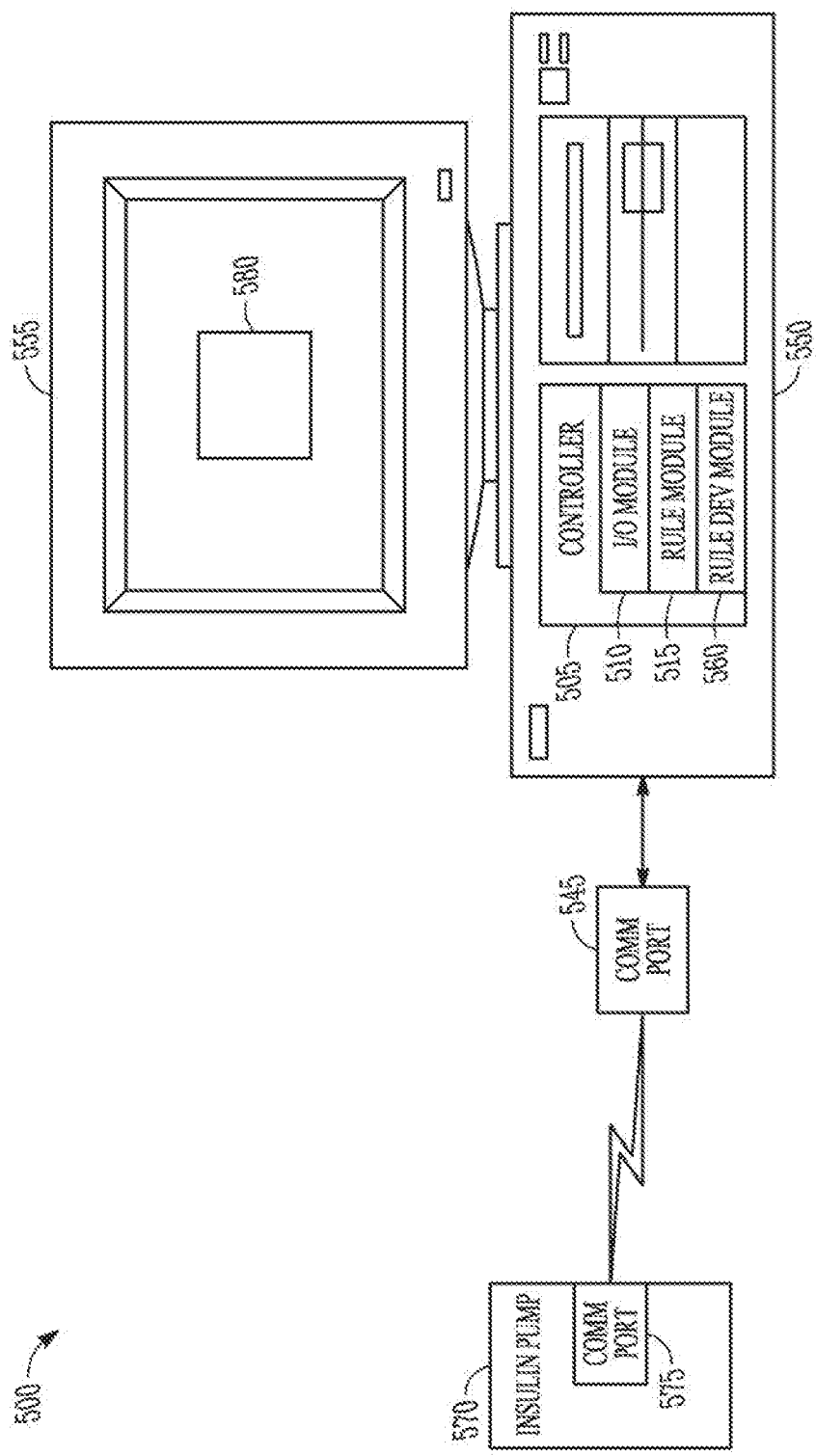
FIG. 5 is a diagram of yet another example of portions of a device to provide assistance in maintaining and adjusting a patient's insulin pump therapy.

FIG. 5 is a diagram of an example of a device 500 to provide assistance in maintaining and adjusting a patient's insulin pump therapy. The device 500 includes a computing device 550. Examples of a computing device 550 include among other things a personal computer (PC), laptop computer, and personal data assistant (PDA). The computing device 550 includes a controller 505. The controller 505 includes an I/O module 510 and a rule module 515. The computing device 550 also includes a user interface 555 that includes a display and may include at least one of a keyboard or keypad and a computer mouse. The computing device 550 further includes a communication port 545 communicatively coupled to the I/O module 510. The device 500 communicates information with an insulin pump 570 via the communication port 545. In some examples, the communication port 545 is a wireless port and the device 500 communicates with the insulin pump 570 using wireless signals, such as a radio frequency (RF) port or infrared (IR) port for example. In some examples, the communication port 545 is a wired port (e.g., a serial port) and the device 500 communicates with the insulin pump using a removable communication cable.

The rule module 515 applies a rule to generate at least one insulin pump setting. The I/O module 510 presents the setting to a user as a suggested insulin pump setting via the user interface 555. The I/O module 510 also presents a request for confirmation of the insulin pump setting. When the I/O module 510 receives a confirmation, such as through the user interface 555 for example, the I/O module 510 communicates the insulin pump setting to the insulin pump 570 via the communication port 545.

As set forth previously, a rule may be customized. In some examples, the controller 505 includes a rule development module 560 to develop a rule via edits received via the I/O module 510. The rule development module 560 is a rule editor that edits existing rules in addition to generating new rules. In some examples, the rule development module 560 displays a representation 580 of the rule when the I/O module 510 is communicatively coupled to the user interface 555. The rule development module 560 converts a manipulation of the displayed representation 580 via the user interface into the edit to the rule.

The rule development module 560 provides doctors or clinical experts the ability to develop and generate a new rule (or rule set) or to modify rules via the user interface 555. The computing device 550 includes software that provides a flexible framework to create or modify rules such as by updating a graphical decision tree or a look-up table for example. The software may be included in a computer readable medium, such as a compact disc (CD) for example, or the software may be downloaded to the computing device 550 from remote storage, such as from a server for example. The computing device 550 uses the communication port 545 to communicate the rule or rule set to the insulin pump 570.

Once a rule is developed, the doctor or clinical expert could publish or otherwise share a rule or set of rules. In some embodiments, rule sets can be stored in remote storage, such as a server for example. The computing device 550 may be connected to a communication network, such as the internet or a cell phone network for example. A doctor or clinical expert may download a rule or rule set from the remote storage and either download the rule set directly from the computing device 550 into the insulin pump device 570 or modify the rule or rule set before downloading the modified rule or rule set to the insulin pump device 570.

Returning to FIG. 4, the controller 405 may include a rule development module. The user interface 430 receives edits to a rule or rule set. The edits are entered into the device 400 manually by the user via the user interface 430. For example, the user may step through the rule with the aid of a display included in the user interface 430. The user may then alter the rule with a keypad included in the user interface 430. For example, the user may enter a new look up table entry using the key pad, or add another branch to a decision tree or edit a branch of the decision tree. In certain examples, an entire new rule or rule set is entered manually into the device 400 via the user interface 430.

In some examples, the device 400 of FIG. 4 or the insulin pump device 570 of FIG. 5 stores data to track effectiveness of a new rule or modified rule. For example, the insulin pump device 570 may track the number of times the blood glucose level of the patient returned to a target blood glucose level or to within a target range of levels after application of the rule. The effectiveness may be displayed as a percentage or as X successes out of Y applications on either a display of the insulin pump device 570 or uploaded and displayed on a separate device, such as the computing device 550 in FIG. 5 for example.

Returning to the device of FIG. 2, in some examples, the rule module 215 assigns weights to corresponding table entries in a rule. For example, a certain type of exercise (e.g. higher intensity) may be weighted higher when determining whether to suggest a different basal rate for the patient during the exercise (versus suggesting a food to eat before exercise of lower intensity). In some examples, the rule module 215 uses one or more fuzzy logic rules to determine the question for display and any recommended action. The fuzzy logic rules may be used to blend any weighted questions, responses, or actions. In some examples, the rule module 215 uses a rule involving application of artificial intelligence methods to determine the questions and the actions to be presented. In some examples, the weighting used by the rule is customizable.

In some examples, the memory 220 stores a database of food options in association with a known amount of nutrient content. The rule module 215 uses the patient health, lifestyle, and demographic information set forth above and generates a suggested database of food options. For example, if the patient lifestyle information indicates that the patient tends to eat high glycemic index foods, or the patient health information indicates that the patient is pregnant, the suggested data base may include mostly low glycemic foods. If the controller 205 is included in a computing device 550 of FIG. 5 or other type of device, that device communicates the suggested database to the insulin pump device 570 where it is stored. If the controller 205 is included in an insulin pump device as in FIG. 4, the controller 405 only displays the suggested portion of the database to a user.

Without an expert system, a pump user may go through several iterations of trial and error in finding appropriate insulin pump settings. In some examples, the device 200 uses blood glucose information as feedback to better tune insulin pump settings. The rule module 215 applies the rule to blood glucose information, such as blood glucose data taken using a blood glucose monitor (GM), to determine one or more insulin pump settings.

The I/O module 210 may present an action for the user to take. In some examples, the action presented may be a prompt for the user to enter blood glucose data into the device, download blood glucose data into the device, or to begin a blood glucose measurement. For example, the action presented may be a prompt to measure blood glucose level from a finger stick and to enter the data into the I/O module 210 through a user interface. In some examples, the device 200 includes a communication port communicatively coupled to the controller 205. The I/O module 210 receives the blood glucose data via the communication port from a second separate device that includes a glucose monitor. In some examples, the communication port includes a wireless communication port. A separate device may obtain the blood glucose data during a test executed using an insulin pump. In some examples, the device 200 includes an insulin pump communicatively coupled to the controller 205.

Figure 6:
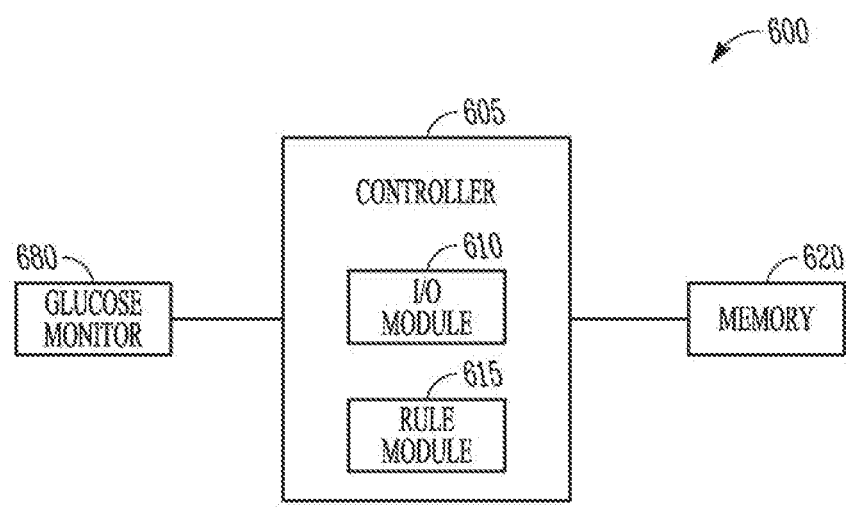
FIG. 6 is a block diagram of a further example of portions of a device to provide assistance in maintaining and adjusting a patient's insulin pump therapy.

In some examples, the device 200 includes a GM. FIG. 6 is a diagram of another example of a device 600 to provide assistance in maintaining and adjusting a patient's insulin pump therapy. The device 600 includes a controller 605 communicatively coupled to a memory 620. The controller 605 includes an I/O module 610 and a rule module 615. The device also includes a GM 680 communicatively coupled to the controller 605. In some examples, the device 600 also includes an insulin pump communicatively coupled to the controller 605.

If the GM 680 is a continuous GM, no action is needed from the user to obtain blood glucose data. A continuous GM includes a blood glucose sensor to produce a blood glucose signal representative of a blood glucose level of the patient. The blood glucose sensor may sense blood glucose concentration from blood or interstitial fluid. The blood glucose sensor circuit may include a sensor interface circuit to sample the blood glucose signal and may provide additional signal processing such as filtering or amplification for example. The blood glucose sensor circuit may provide a sampled blood glucose data to the I/O module 610. A description of a blood glucose sensor circuit can be found in Steil et al., U.S. Pat. No. 6,558,351, filed Jun. 1, 2000.

Returning to FIG. 2, the action presented by the I/O module 210 may include prompting the user to begin a test or a series of tests in which blood glucose data is monitored and received into the device 200 via the I/O module 210. A test may be executed using an insulin pump. The rule module 215 applies the rule to at least one of the blood glucose data and the patient information to determine an insulin pump setting. In some examples, the rule module 215 generates an insulin pump setting that includes a target blood glucose level for the patient. The target blood glucose level may be a range of blood glucose levels.

Because a patient's basal insulin needs may change over time, such as with weight change or with a change in fitness level, basal rate testing may be performed periodically to ensure that an appropriate basal rate is being delivered by an insulin pump. Based on blood glucose data (e.g., the blood glucose level of the patient is not at the target blood glucose level), the rule module 215 may determine from the rule that a basal rate test should be run (by either the insulin pump included with the device 200 or a separate device). The I/O module 210 may present (such as by display) a suggestion to the user to execute a basal rate test. As a result of the basal rate test, the rule module 215 generates one or more basal rate patterns or profiles. The I/O module 210 may display a recommendation to change a programmable basal rate pattern of the insulin pump. Descriptions of devices and methods that perform a basal rate test are found in Blomquist et al., "Basal Rate Testing Using Frequent Blood Glucose Input," U.S. patent application Ser. No. 11/685,617, filed Mar. 13, 2007, which is incorporated herein by reference.

If a carbohydrate ratio is too small, the insulin pump may determine a carbohydrate bolus that is too large for the carbohydrates consumed. This may cause a low blood glucose level within a few hours of the carbohydrate bolus (e.g., the blood glucose level drops below 70 mg/dl). If a carbohydrate bolus is too large, the insulin pump may determine a carbohydrate bolus that is too small for the carbohydrates consumed. This may cause a high blood glucose level within a few hours of a carbohydrate bolus.

Based on the blood glucose data, the rule module 215 may determine that a recommendation to run a carbohydrate ratio test should be presented. As a result of the carbohydrate ratio test, the rule module 215 may generate a new carbohydrate ratio. The I/O module 210 may present a recommendation to change the carbohydrate ratio programmed in the insulin pump. In some examples, the rule module 215 may generate a carbohydrate insulin bolus pattern or profile to be delivered by the insulin pump. For example, the I/O module 210 may display a recommended carbohydrate bolus pattern that includes an extended carbohydrate bolus or a combination bolus. Descriptions of devices and methods that perform a carbohydrate ratio test are found in Blomquist, "Carbohydrate Ratio Testing Using Frequent Blood Glucose Input," U.S. patent application Ser. No. 11/679,712, filed Feb. 27, 2007, which is incorporated herein by reference.

It is important for an insulin pump to use an effective correction factor. If a correction factor for a pump is set too high, the blood glucose may not actually be dropping as much as estimated and could lead to high blood glucose levels. If the correction factor is set too low, a correction bolus may provide too much insulin and result in a low blood glucose level.

Based on the blood glucose data, the rule module 215 may apply the rule to the blood glucose data and present a recommendation that the user initiate a correction factor test. As a result of the correction factor test, the rule module 215 may generate a new a correction factor. The I/O module 210 may present a recommendation to change the correction factor programmed in the insulin pump. In some examples, the rule module 215 may generate an insulin correction bolus pattern or profile. For example, the I/O module 210 may display a recommended correction bolus such as a pattern including different correction factors for different times of the day for example. Descriptions of devices and methods that perform a carbohydrate ratio test are found in Blomquist et al., "Correction Factor Testing Using Frequent Blood Glucose Input," U.S. patent application Ser. No. 11/626,653, filed Jan. 24, 2007, which is incorporated herein by reference. If the device 200 includes an insulin pump, the controller 205 may executes one of the tests described.

The examples set forth above involved the device 200 recommending an action for the user to take based on the blood glucose data received into the device. In some examples, the rule module 215 may use the blood glucose data to first generate a question to be presented by the I/O module 210 before presenting an action. The rule module 215 generates the suggested insulin pump setting from application of the rule to the blood glucose data and patient information received in response to the question. For example, if the blood glucose data indicates blood glucose is low, the rule may include a look up table having a question as to whether the patient had a high activity level. If the device 200 receives a response through a user interface that the activity level was high, the look up table may include a recommended action corresponding to a table entry for low blood glucose and high activity. The table entry may include a recommended action that the patient eat before the activity or lower a programmable basal rate of insulin before, during, or after the activity.

In some examples, the controller 205 determines a rate of change of a blood glucose level of the patient from the blood glucose data. As an illustrative example, the controller 205 may determine that the blood glucose concentration level is increasing or decreasing at a rate of 2 to 4 mg/dl/min (milligrams per deciliter per minute). The rule module 215 may apply one or more rules to the rate of change of a blood glucose level to generate a suggested insulin pump setting. If the blood glucose level is high and increasing at a certain rate, the rule module 215 may apply the rule to generate an insulin correction bolus pattern.

The action presented by the I/O module 210 may be a test or tests that include a variety of steps. The tests may be included in the rule module 215 and are designed to obtain data or other information that is analyzed by the rule. The tests may occur over a series of days. For example, during the test the device 200 may instruct the insulin pump user to skip breakfast the first day, skip lunch the second day, and skip dinner the third day. The device 200 may display an action for the user that includes taking blood glucose measurements at specified times in the test, such as pre-meal, post-meal, and while fasting for example. The device 200 may ask the user to perform or not perform certain activities (e.g., exercise) during the testing. The device may present an action to the user to eat specific portions of food having specific nutritional content. As part of the test, the device 200 may ask the user to input patient information into the device 200 (e.g., through the user interface, or through a second separate device that communicates with the device 200 via a communication port). The patient information may include health information, stress level information, or other information pertinent to later test analysis.

After the testing, the device 200 presents one or more questions to the user. The questions and responses from the user are part of a post-test patient interview by the device 200. The information from the patient interview and the blood glucose data are then analyzed. The rule module 215 applies the rule to the responses during the interview, the blood glucose data obtained as part of the test, and any other test data. The rule module 215 generates changes to insulin therapy parameters. In some examples, the changes are presented to the user, and the user has the option of accepting the changes.

If the device 200 includes an insulin pump, the changes are adopted by the device 200. If the device is a computing device such as in FIG. 5, or a device that includes a GM that is separate from the insulin pump, the changes may be communicated to the insulin pump. According to some examples the functions can be accomplished using multiple devices. For example, a first device may guide the patient through the test or tests. This device may include an insulin pump such as the device 400 in FIG. 4. The patient interview and analysis may be done by a second device such as the device 500 in FIG. 5.

As set forth previously, a rule or set of rules may be customized, such as by a rule development module included in the controller 205 for example. In some examples, all or substantially all aspects of the rule are customizable, including the type of tests to run, the sequence of tests to run, the steps in the tests, and the criteria for making changes. An expert in the treatment of diabetes would customize the rules to suit their standard of practice.

According to some embodiments, the device 200 may present changes other than insulin pump therapy parameters. In some examples, the rule module 215 may generate a recommend change to a patient lifestyle, such as a recommendation to exercise more or to reduce smoking. The I/O module 210 presents the recommend changes to the lifestyle of the patient. In some examples, the rule module 215 may generate a recommend change to a patient diet, such as a recommendation to eat foods having a lower glycemic index or to consume less alcohol.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

The invention claimed is:

1. A system comprising:
a pump configured to deliver insulin;
an input configured to receive sensor glucose data representative of a blood glucose level of a user from a continuous glucose monitor via a wireless connection; and
a controller communicatively coupled to the pump and the input, the controller configured to:
monitor the sensor glucose data from the continuous glucose monitor;
determine a rate of change of the blood glucose level of the user from the sensor glucose data;
determine, based on a current blood glucose level of the user and the rate of change of the blood glucose level, that a correction bolus should be generated;
automatically calculate the correction bolus; and
cause the pump to deliver the correction bolus to the user.

2. The system of claim 1, wherein the controller is further configured to compare the current blood glucose level of the user and the rate of change to a predetermined high blood glucose level.

3. The system of claim 1, wherein the controller is configured to automatically deliver the correction bolus.

4. The system of claim 1, wherein the controller is further configured to present a recommendation to deliver the correction bolus on a user interface and to deliver the correction bolus only after receiving a confirmation in response to the recommendation.

5. The system of claim 1, wherein the controller is configured to determine, based on a current blood glucose level of the user and the rate of change of the blood glucose level, that a correction bolus should be generated based on a comparison to a target blood glucose level.

6. The system of claim 1, wherein the controller is configured to determine, based on a current blood glucose level of the user and the rate of change of the blood glucose level, that a correction bolus should be generated if the blood glucose level is high and increasing at a certain rate.

7. The system of claim 1, wherein the controller is further configured to provide a notification to the user regarding the correction bolus.

8. The system of claim 1, wherein the controller, the input and the pump are part of a common device.

9. The system of claim 1, wherein the controller and the input are part of a handheld device that is separate from the pump.

10. A system comprising:
a pump configured to deliver insulin;
an input configured to receive sensor glucose data representative of a blood glucose level of a user from a continuous glucose monitor via a wireless connection; and a controller communicatively coupled to the pump and the input, the controller configured to:
- monitor the sensor glucose data from the continuous glucose monitor;
- determine a rate of change of the blood glucose level of the user from the sensor glucose data;
- determine, based on a current blood glucose level of the user and the rate of change of the blood glucose level, that a current insulin delivery pattern should be modified;
- automatically calculate a modification to the insulin delivery pattern; and
- cause the pump to employ the modified insulin delivery pattern.

11. The system of claim 10, wherein when the controller determines that the current insulin delivery pattern should be modified and the rate of change indicates that the blood glucose level is increasing, the controller is configured to calculate the modification to the insulin delivery pattern by calculating an insulin correction bolus.

12. The system of claim 10, wherein when the controller determines that the current insulin delivery pattern should be modified and the rate of change indicates that the blood glucose level is decreasing, the controller is configured to calculate the modification to the insulin delivery pattern by reducing an amount of insulin delivered.

13. The system of claim 10, wherein the controller is further configured to compare the current blood glucose level of the user to a target blood glucose level.

14. The system of claim 13, wherein the controller comparing the current blood glucose level to a target blood glucose level includes comparing the current blood glucose level to a target range of blood glucose levels.

15. The system of claim 10, wherein the controller is configured to automatically deliver the modified insulin delivery pattern.

16. The system of claim 10, wherein the controller is further configured to present a recommendation to modify the insulin delivery pattern on a user interface and to deliver the modified insulin delivery pattern only after receiving a confirmation in response to the recommendation.

17. The system of claim 10, wherein the controller is further configured to provide a notification to the user regarding the modification to the insulin delivery pattern.

18. The system of claim 10, wherein the controller, the input and the pump are part of a common device.

19. The system of claim 10, wherein the controller and the input are part of a handheld device that is separate from the pump.

* * * * *